United States Patent
Pawlowski et al.

(10) Patent No.: US 11,938,181 B2
(45) Date of Patent: Mar. 26, 2024

(54) IDENTIFYING PATIENT POPULATIONS VULNERABLE TO VIRAL INFECTION AND METHODS OF INDUCING HETEROLOGOUS IMMUNITY IN SAME

(71) Applicant: nference, Inc., Cambridge, MA (US)

(72) Inventors: Colin Pawlowski, Boston, MA (US); Venkataramanan Soundararajan, Andover, MA (US); Arjun Puranik, San Jose, CA (US); Murali Aravamudan, Andover, MA (US)

(73) Assignee: nference, Inc., Cambridge, MA (US)

( * ) Notice: Subject to any disclaimer, the term of this patent is extended or adjusted under 35 U.S.C. 154(b) by 0 days.

(21) Appl. No.: 17/371,555

(22) Filed: Jul. 9, 2021

(65) Prior Publication Data

US 2022/0016233 A1 Jan. 20, 2022

Related U.S. Application Data

(60) Provisional application No. 63/055,751, filed on Jul. 23, 2020, provisional application No. 63/050,349, filed on Jul. 10, 2020.

(51) Int. Cl.
| | | |
|---|---|---|
| *A61K 39/215* | (2006.01) | |
| *A61K 39/00* | (2006.01) | |
| *A61K 39/09* | (2006.01) | |
| *A61K 39/116* | (2006.01) | |
| *A61K 39/145* | (2006.01) | |
| *A61K 39/25* | (2006.01) | |
| *A61K 39/29* | (2006.01) | |
| *A61K 39/295* | (2006.01) | |
| *A61P 31/14* | (2006.01) | |
| *A61P 37/04* | (2006.01) | |

(52) U.S. Cl.
CPC .......... *A61K 39/215* (2013.01); *A61K 39/092* (2013.01); *A61K 39/116* (2013.01); *A61K 39/145* (2013.01); *A61K 39/25* (2013.01); *A61K 39/29* (2013.01); *A61K 39/292* (2013.01); *A61K 39/295* (2013.01); *A61P 31/14* (2018.01); *A61P 37/04* (2018.01); *A61K 2039/55* (2013.01)

(58) Field of Classification Search
CPC .. A61K 39/215; A61K 39/092; A61K 39/116; A61K 39/145; A61K 39/25; A61K 39/29; A61K 39/292; A61K 39/295; A61K 2039/55; A61K 39/102; A61K 39/12; A61K 2039/58; A61P 31/14; A61P 37/04; C12N 2710/16734; C12N 2730/10134; C12N 2760/18434; C12N 2760/18734; C12N 2770/32434; C12N 2770/32634; C12N 2770/36234; Y02A 50/30
See application file for complete search history.

(56) References Cited

FOREIGN PATENT DOCUMENTS

| WO | WO-2021161043 A1 * | 8/2021 |
| WO | WO-2021228363 A1 * | 11/2021 |
| WO | WO-2021258008 A1 * | 12/2021 |
| WO | WO-2022066926 A1 * | 3/2022 |
| WO | WO2022176068 A1 * | 8/2022 |
| WO | WO2022176920 A1 * | 8/2022 |

OTHER PUBLICATIONS

Sarialioglu F, Belen Apak FB, Haberal M. Can Hepatitis A Vaccine Provide Protection Against COVID-19? Exp Clin Transplant. Apr. 2020;18(2):141-143. (Year: 2020).*
Jehi L, Ji X, Milinovich A, Erzurum S, Rubin BP, Gordon S, Young JB, Kattan MW. Individualizing Risk Prediction for Positive Coronavirus Disease 2019 Testing: Results From 11,672 Patients. Chest. Oct. 2020;158(4):1364-1375. Epub Jun. 10, 2020. (Year: 2020).*
Kandeil A, Gomaa MR, El Taweel A, Mostafa A, Shehata M, Kayed AE, Kutkat O, Moatasim Y, Mahmoud SH, Kamel MN, Shama NMA, et. al. Common childhood vaccines do not elicit a cross-reactive antibody response against SARS-CoV-2. PLoS One. Oct. 28, 2020;15(10):e0241471. (Year: 2020).*
Netea MG, Giamarellos-Bourboulis EJ, Domínguez-Andrés J, Curtis N, van Crevel R, van de Veerdonk FL, Bonten M. Trained Immunity: a Tool for Reducing Susceptibility to and the Severity of SARS-CoV-2 Infection. Cell. May 28, 2020;181(5):969-977. Epub May 4, 2020. (Year: 2020).*
Anbarasu A, Ramaiah S, Livingstone P. Vaccine repurposing approach for preventing COVID 19: can MMR vaccines reduce morbidity and mortality? Hum Vaccin Immunother. Sep. 1, 2020;16(9):2217-2218. Epub Jun. 5, 2020. (Year: 2020).*
Fidel PL Jr, Noverr MC. Could an Unrelated Live Attenuated Vaccine Serve as a Preventive Measure to Dampen Septic Inflammation Associated with COVID-19 Infection? mBio. Jun. 19, 2020;11(3):e00907-20. (Year: 2020).*
FLUAD® Seqirus Inc. Package insert, Oct. 14, 2020. (Year: 2020).*
Sanofi Pasteur 450/477 FLUZONE® Quadrivalent Package insert, 2022-2023 Formula, Rev. Jul. 2022. (Year: 2022).*
Smetana J, Chlibek R, Shaw J, Splino M, Prymula R. Influenza vaccination in the elderly. Hum Vaccin Immunother. Mar. 4, 2018;14(3):540-549. doi: 10.1080/21645515.2017.1343226. Epub Aug. 4, 2017. PMID: 28708957; PMCID: PMC5861798. (Year: 2017).*
Merriam-Webster Online Dictionary. "geriatric". Accessed Mar. 16, 2023. https://www.merriam-webster.com/dictionary/geriatric. (Year: 2023).*
Ietto G. SARS-CoV-2: Reasons of epidemiology of severe ill disease cases and therapeutic approach using trivalent vaccine (tetanus, diphtheria and Bordetella pertussis). Med Hypotheses. Aug. 2020;141:109779. doi: 10.1016/j.mehy.2020.109779. Epub Apr. 22, 2020. (Year: 2020).*

(Continued)

*Primary Examiner* — Rachel B Gill
(74) *Attorney, Agent, or Firm* — Caldwell Intellectual Property Law

(57) ABSTRACT

This application relates to methods for assessing patient populations and determining subpopulations vulnerable to viral infection, methods of reducing the risk of infection and/or inducing heterologous immunity to said viral infection.

16 Claims, 10 Drawing Sheets

(56) References Cited

OTHER PUBLICATIONS

Cristiani L, Mancino E, Matera L, Nenna R, Pierangeli A, Scagnolari C, Midulla F. Will children reveal their secret? The coronavirus dilemma. Eur Respir J. Apr. 23, 2020;55(4):2000749. doi: 10.1183/13993003.00749-2020. PMID: 32241833; PMCID: PMC7113798. (Year: 2020).*

Covián C, Retamal-Díaz A, Bueno SM, Kalergis AM. Could BCG Vaccination Induce Protective Trained Immunity for SARS-CoV-2? Front Immunol. May 8, 2020;11:970. doi: 10.3389/fimmu.2020.00970. PMID: 32574258; PMCID: PMC7227382. (Year: 2020).*

Kerboua KE. The perplexing question of trained immunity vs adaptive memory in COVID-19. J Med Virol. Oct. 2020;92(10):1858-1863. doi: 10.1002/jmv.26083. Epub Jul. 14, 2020. PMID: 32470151. (Year: 2020).*

Tayar E, Abdeen S, Abed Alah M, Chemaitelly H, Bougmiza I, Ayoub HH, et al. Effectiveness of influenza vaccination against SARS-CoV-2 infection among healthcare workers in Qatar. Prepublished on May 10, 2020 in medRxiv 2022.05.09.22274802; doi: https://doi.org/10.1101/2022.05.09.22274802. (Year: 2020).*

Liu Y, Du X, Chen J, Jin Y, Peng L, Wang HHX, Luo M, Chen L, Zhao Y. Neutrophil-to-lymphocyte ratio as an independent risk factor for mortality in hospitalized patients with COVID-19. J Infect. Jul. 2020;81(1):e6-e12. Epub Apr. 10, 2020. (Year: 2020).*

Li X, Xu S, Yu M, Wang K, Tao Y, Zhou Y, Shi J, Zhou M, Wu B, Yang Z, Zhang C, Yue J, Zhang Z, Renz H, Liu X, Xie J, Xie M, Zhao J. Risk factors for severity and mortality in adult COVID-19 inpatients in Wuhan. J Allergy Clin Immunol. Jul. 2020;146(1):110-118. Epub Apr. 12, 2020. (Year: 2020).*

Chen X, Tang Y, Mo Y, Li S, Lin D, Yang Z, Yang Z, Sun H, Qiu J, Liao Y, Xiao J, Chen X, Wu X, Wu R, Dai Z. A diagnostic model for coronavirus disease 2019 (COVID-19) based on radiological semantic and clinical features: a multi-center study. Eur Radiol. Sep. 2020;30(9):4893-4902. Epub Apr. 16, 2020. (Year: 2020).*

Li Q, Tang B, Bragazzi NL, Xiao Y, Wu J. Modeling the impact of mass influenza vaccination and public health interventions on COVID-19 epidemics with limited detection capability. Math Biosci. Jul. 2020;325:108378. doi: 10.1016/j.mbs.2020.108378. Epub May 16, 2020. (Year: 2020).*

Azar KMJ, Shen Z, Romanelli RJ, Lockhart SH, Smits K, Robinson S, Brown S, Pressman AR. Disparities in Outcomes Among COVID-19 Patients in a Large Health Care System in California. Health Aff (Millwood). Jul. 2020;39(7):1253-1262. doi: 10.1377/hlthaff.2020.00598. Epub May 21, 2020. PMID: 32437224. (Year: 2020).*

Rong H, Lai X, Ma X, Hou Z, Li S, Jing R, Zhang H, Peng Z, Feng L, Fang H. Seasonal Influenza Vaccination and Recommendation: The Difference between General Practitioners and Public Health Workers in China. Vaccines (Basel). May 31, 2020;8(2):265. (Year: 2020).*

Günther Fink, Nina Orlova-Fink, Tobias Schindler, Sandra Grisi, Ana Paula Ferrer, Claudia Daubenberger, Alexandra Brentani. Inactivated trivalent influenza vaccine is associated with lower mortality among Covid-19 patients in Brazil. Jul. 1, 2020. medRxiv 2020.06.29.20142505. (Year: 2020).*

* cited by examiner

IDENTIFYING PATIENT POPULATIONS VULNERABLE TO VIRAL INFECTION AND METHODS OF INDUCING HETEROLOGOUS IMMUNITY IN SAME

CROSS-REFERENCE TO RELATED APPLICATIONS

This application claims the benefit of U.S. Provisional Application Nos. 63/055,751, filed Jul. 23, 2020, and 63/050,349, filed Jul. 10, 2020, which are hereby incorporated by reference in their entireties.

BACKGROUND

Since the genome for severe acute respiratory syndrome coronavirus 2 (SARS-CoV-2) was released on Jan. 11, 2020, scientists around the world have been racing to develop a vaccine.[1] However, vaccine development is a long and expensive process, which takes on average over 10 years under ordinary circumstances.[2] Even for the epidemics of the past decade, including SARS, Zika, and Ebola, vaccines were not available before the virus spread was largely contained.[3]

Conventionally vaccinations are intended to train the adaptive immune system by generating an antigen-specific immune response. However, studies are also demonstrating that certain vaccines lead to protection against other infections. For instance, vaccination against smallpox showed protection against measles and whooping cough4. Live vaccinia virus was successfully used against smallpox. Due to the urgent need to reduce the spread of SARS-CoV-2, scientists are turning to alternate methods to reduce the spread, such as repurposing existing vaccines. There are multiple ongoing clinical studies to determine whether or not existing vaccines may provide some protection against risk of SARS-CoV-2 infection, which is the virus that is the cause of the global coronavirus disease 2019 (COVID-19) pandemic. For example, there are some hypotheses that the Bacillus Calmette-Guérin (BCG) and live poliovirus vaccines may provide some protective effect against COVID-19 infection.[5,6] There are also several ongoing/recruiting clinical trials testing the protective effects of existing vaccines against COVID-19 infection, including: Polio[7], Measles-Mumps-Rubella vaccine[8], Influenza vaccine[9], and BCG vaccine[10,11,12,13]. Thus, in the absence of available vaccine, the ability to assess potential heterologous immunity from existing vaccines in specific subpopulations may allow for the identification and subsequent treatment of vulnerable subjects. What is more, such analysis allows for the identification of characteristics and qualities associated with existing cross-protecting vaccines, and thus contribute to the design of novel vaccines, including subpopulation and/or subject specific vaccines.

SUMMARY

The present disclosure is based, at least in part, on the analysis of patient-specific data (e.g., data from the Mayo Clinic electronic health record (EHR) database) to systematically assess the cross-protective effects of existing vaccines against SARS-CoV-2 infection for 1 year, 2 year, and 5 year time horizons. For each vaccine, propensity score matching was used to control for potential confounding variables which could account for observed differences in rates of SARS-CoV-2 infection. Such variables included geographic COVID-19 incidence rates and testing rates, demographics, comorbidities, and immunization with other vaccines (e.g., number of other vaccinations).

In some aspects of the invention, disclosed herein are methods for reducing the risk of a subject acquiring or fully presenting a disease case by SARS-CoV-2 infection, comprising determining the immunization history of the subject, identifying whether the subject has not received at least one of a haemophilus influenzae type B (Hib) vaccine, a geriatric flu vaccine, a diphtheria-pertussis-tetanus vaccine, or a measles-mumps-rubella vaccine, and administering at least one such vaccine to the subject. In certain aspects, provided herein are methods inducing a heterologous immune response to SARS-CoV-2 infection in a subject, comprising determining the immunization history of the subject, identifying whether the subject has not received at least one of a haemophilus influenzae type B (Hib) vaccine, a geriatric flu vaccine, a diphtheria-pertussis-tetanus vaccine, or a measles-mumps-rubella vaccine, and administering at least one such vaccine to the subject. In some embodiments, the subject has not received at least one of said vaccines within the past 1 to 5 years. In preferred embodiments, the subject has not received at least one of said vaccines within the past year. In some embodiments, the subject has not received at least one of said vaccines within the past 2 years. In further embodiments, the subject has not received at least one of said vaccines within the past 5 years.

In some aspects of the invention, disclosed herein are methods for reducing the risk of a subject acquiring or fully presenting a disease case by SARS-CoV-2 infection, comprising determining the immunization history of the subject, identifying whether the subject has not received at least one of a hepatitis A/hepatitis B vaccine, a haemophilus influenzae type B (Hib) vaccine, a pneumococcal vaccine, a diphtheria-pertussis-tetanus vaccine, or a polio vaccine, and administering at least one such vaccine to the subject. In certain aspects, provided herein are methods inducing a heterologous immune response to SARS-CoV-2 infection in a subject, comprising determining the immunization history of the subject, identifying whether the subject has not received at least one of a hepatitis A/hepatitis B vaccine, a haemophilus influenzae type B (Hib) vaccine, a pneumococcal vaccine, a diphtheria-pertussis-tetanus vaccine, or a polio vaccine, and administering at least one such vaccine to the subject. In some embodiments, the subject has not received at least one of said vaccines within the past 1 to 5 years. In certain embodiments, the subject has not received at least one of said vaccines within the past year. In preferred embodiments, the subject has not received at least one of said vaccines within the past 2 years. In further embodiments, the subject has not received at least one of said vaccines within the past 5 years.

In some aspects of the invention, disclosed herein are methods for reducing the risk of a subject acquiring or fully presenting a disease case by SARS-CoV-2 infection, comprising determining the immunization history of the subject, identifying whether the subject has not received at least one of a polio vaccine, a pneumococcal vaccine, a geriatric flu vaccine, a varicella vaccine, an RZV zoster vaccine, or a diphtheria-pertussis-tetanus vaccine, and administering at least one such vaccine to the subject. In certain aspects, provided herein are methods inducing a heterologous immune response to SARS-CoV-2 infection in a subject, comprising determining the immunization history of the subject, identifying whether the subject has not received at least one of a polio vaccine, a pneumococcal vaccine, a geriatric flu vaccine, a varicella vaccine, an RZV zoster vaccine, or a diphtheria-pertussis-tetanus vaccine, and administering at least one such vaccine to the subject. In some embodiments, the subject has not received at least one of said vaccines within the past 1 to 5 years. In some embodiments, the subject has not received at least one of said vaccines within the past year. In certain embodiments, the subject has not received at least one of said vaccines within the past 2 years. In preferred embodiments, the subject has not received at least one of said vaccines within the past 5 years.

In certain aspects of the invention, disclosed herein are methods for the identification and stratification of a subject at risk of SARS-CoV-2 infection comprising determining the immunization history of the subjects, demographic covariates of the subject, and identifying whether the subject has not received at least one of a polio vaccine, a pneumococcal vaccine, a geriatric flu vaccine, a varicella vaccine, an RZV zoster vaccine, or a diphtheria-pertussis-tetanus vaccine, and administering at least one such vaccine to the corresponding subject. In some embodiments, the subject has not received at least one of said vaccines within the past 1 to 5 years. In some embodiments, the subject has not received at least one of said vaccines within the past year. In certain embodiments, the subject has not received at least one of said vaccines within the past 2 years. In preferred embodiments, the subject has not received at least one of said vaccines within the past 5 years.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

DETAILED DESCRIPTION

Figure 1:
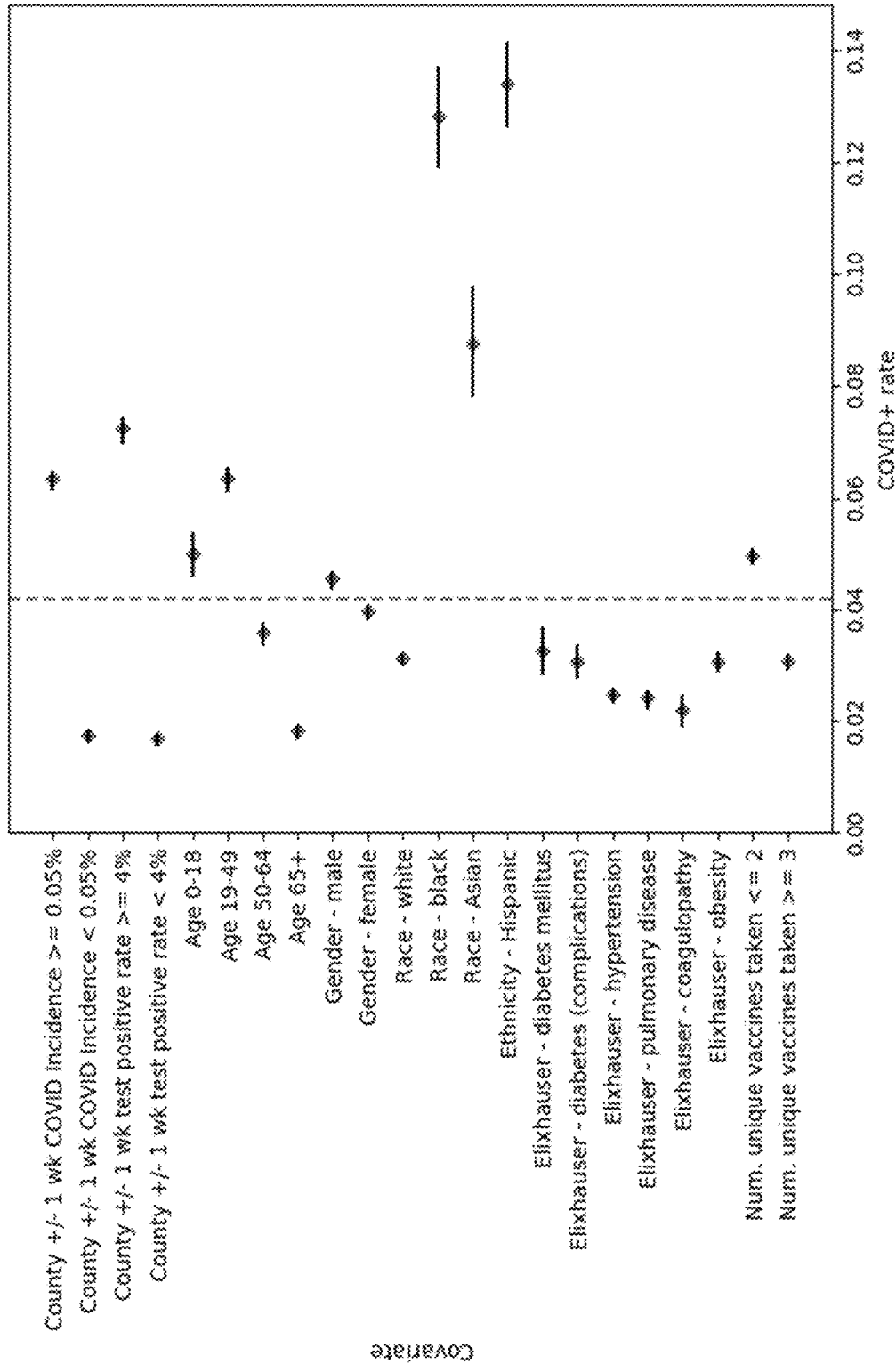
FIG. 1 shows for a selection of covariates that were matched, the COVID+ rate among patients who have the covariate, along with 95% confidence intervals. The population COVID+ rate (dotted line) of 4.4% was included as a reference against which to compare these rates. Continuous covariates were partitioned into buckets.

Disclosed herein is a systematic analysis to determine whether or not one or more existing (e.g., routinely prescribed) vaccines in the United States are associated with decreased rates of SARS-CoV-2 infection and thus have protective effects. The analysis was performed on data from 138,246 patients from the Mayo Clinic electronic health record (EHR) database who received PCR tests for SARS-CoV-2 between Feb. 15, 2020 and Jul. 14, 2020 and have at least one ICD diagnostic code recorded in the past five years. Relative SARS-CoV-2 infection rates for subsets of the study population with particular clinical covariates were assessed. The rates of SARS-CoV-2 infection were much higher in Black, Asian, and Hispanic racial and ethnic subgroups compared to the overall study population. The rates of SARS-CoV-2 infection were also higher in patients with pre-existing conditions (e.g. hypertension, diabetes, obesity) due to the fact that these patients receive higher rates of PCR tests. Given this study population, the rates of SARS-CoV-2 infection were assessed among patients who did and did not receive one of 20 vaccines in the past 1, 2, and 5 years relative to the date of PCR testing.

First, the overall association of the vaccines with lower rates of SARS-CoV-2 infection were assessed. Propensity score matching was used to construct negative control cohorts for each of the vaccinated populations at the 1 year, 2 year, and 5 year time horizons, which are balanced in covariates including: demographics, county-level incidence and testing rates for SARS-CoV-2, comorbidities, and number of other vaccines taken in the past 5 years. COVID-19 incidence rates between each of the vaccinated cohorts were compared to corresponding matched, unvaccinated cohorts that have similar clinical characteristics.

Second, statistical analyses to identify differential associations with lower rates of SARS-CoV-2 infection were run for each vaccine in age and race stratified subgroups. For each vaccine at the 5 year time horizon, the difference in SARS-CoV-2 infection rate between the vaccinated and unvaccinated cohorts were computed for each of the age and race stratified subgroups. The output of these statistical tests was used to identify vaccines which may provide protection against COVID-19 for particular subsets of the population.

For example, after controlling for confounding variables as disclosed herein (e.g., geographic SARS-CoV-2 incidence and testing rates, demographics, comorbidities, and number of other vaccinations), the relative risks of SARS-CoV-2 infection for the pneumococcal (general) vaccinated cohort are 0.83 (95% CI: (0.69, 0.99), p-value: 0.09) for the 1 year time horizon, 0.83 for the 2 year time horizon (95% CI: (0.72, 0.95), p-value: 0.03), and 0.82 for the 5 year time horizon (sample size: 18,034, p-value: 4.7e-3). Furthermore, age and race stratified analyses revealed significant differential SARS-CoV-2 rates among black patients who have taken one of the following vaccines in the past 5 years: pneumococcal (general) (relative risk: 0.48, 95% CI: (0.35, 0.66), p-value: 3.5e-4), pneumococcal conjugate (PCV13) (relative risk: 0.42, 95% CI: (0.29, 0.63), p-value: 3.5e-4), or RZV Zoster (relative risk: 0.36, 95% CI: (0.20, 0.66), p-value: 8.8e-3). These findings suggest that additional pre-clinical and prospective clinical studies are warranted to assess the protective effects of existing non-COVID-19 vaccines and explore underlying immunologic mechanisms.

Finally, a series of sensitivity analyses were run to evaluate whether or not the results could have been biased from unobserved confounders or other factors. Pre-existing immunity from cross-protection may be mitigating the risk of SARS-CoV-2 infection in specific subpopulations via immunologic mechanisms that remain to be uncovered.

Thus, in some aspects of the invention, disclosed herein are methods for reducing the risk of a subject acquiring or fully presenting a disease case by SARS-CoV-2 infection, comprising determining the immunization history of the subject, identifying whether the subject has not received at least one of a haemophilus influenzae type B (Hib) vaccine, a geriatric flu vaccine, a diphtheria-pertussis-tetanus vaccine, or a measles-mumps-rubella vaccine, and administering at least one such vaccine to the subject. In certain aspects, provided herein are methods inducing a heterologous immune response to SARS-CoV-2 infection in a subject, comprising determining the immunization history of the subject, identifying whether the subject has not received at least one of a haemophilus influenzae type B (Hib) vaccine, a geriatric flu vaccine, a diphtheria-pertussis-tetanus vaccine, or a measles-mumps-rubella vaccine, and administering at least one such vaccine to the subject. In some embodiments, the subject has not received at least one of said vaccines within the past 1 to 5 years. In preferred embodiments, the subject has not received at least one of said vaccines within the past year. In some embodiments, the subject has not received at least one of said vaccines within the past 2 years. In further embodiments, the subject has not received at least one of said vaccines within the past 5 years.

Similarly, in some aspects of the invention, disclosed herein are methods for reducing the risk of a subject acquiring or fully presenting a disease case by SARS-CoV-2 infection, comprising determining the immunization history of the subject, identifying whether the subject has not received at least one of a hepatitis A/hepatitis B vaccine, a haemophilus influenzae type B (Hib) vaccine, a pneumococcal vaccine, a diphtheria-pertussis-tetanus vaccine, or a polio vaccine, and administering at least one such vaccine to the subject. In certain aspects, provided herein are methods inducing a heterologous immune response to SARS-CoV-2 infection in a subject, comprising determining the immunization history of the subject, identifying whether the subject has not received at least one of a hepatitis A/hepatitis B vaccine, a haemophilus influenzae type B (Hib) vaccine, a pneumococcal vaccine, a diphtheria-pertussis-tetanus vaccine, or a polio vaccine, and administering at least one such vaccine to the subject. In some embodiments, the subject has not received at least one of said vaccines within the past 1 to 5 years. In certain embodiments, the subject has not received at least one of said vaccines within the past year. In preferred embodiments, the subject has not received at least one of said vaccines within the past 2 years. In further embodiments, the subject has not received at least one of said vaccines within the past 5 years.

In certain aspects of the invention, disclosed herein are methods for reducing the risk of a subject acquiring or fully presenting a disease case by SARS-CoV-2 infection, comprising determining the immunization history of the subject, identifying whether the subject has not received at least one of a polio vaccine, a pneumococcal vaccine, a geriatric flu vaccine, a varicella vaccine, an RZV zoster vaccine, or a diphtheria-pertussis-tetanus vaccine, and administering at least one such vaccine to the subject. In certain aspects, provided herein are methods inducing a heterologous immune response to SARS-CoV-2 infection in a subject, comprising determining the immunization history of the subject, identifying whether the subject has not received at least one of a polio vaccine, a pneumococcal vaccine, a geriatric flu vaccine, a varicella vaccine, an RZV zoster vaccine, or a diphtheria-pertussis-tetanus vaccine, and administering at least one such vaccine to the subject. In some embodiments, the subject has not received at least one of said vaccines within the past 1 to 5 years. In some embodiments, the subject has not received at least one of said vaccines within the past year. In certain embodiments, the subject has not received at least one of said vaccines within the past 2 years. In preferred embodiments, the subject has not received at least one of said vaccines within the past 5 years.

In certain aspects of the invention, disclosed herein are methods for the identification and stratification of a subject at risk of SARS-CoV-2 infection comprising determining the immunization history of the subjects, demographic covariates of the subject, and identifying whether the subject has not received at least one of a polio vaccine, a pneumococcal vaccine, a geriatric flu vaccine, a varicella vaccine, an RZV zoster vaccine, or a diphtheria-pertussis-tetanus vaccine, and administering at least one such vaccine to the corresponding subject. In some embodiments, the subject has not received at least one of said vaccines within the past 1 to 5 years. In some embodiments, the subject has not received at least one of said vaccines within the past year. In certain embodiments, the subject has not received at least one of said vaccines within the past 2 years. In preferred embodiments, the subject has not received at least one of said vaccines within the past 5 years.

The methods disclosed herein may comprise administering a combination vaccine. In certain embodiments, the pneumococcal vaccine to be administered is a pneumococcal conjugate vaccine, such as PCV13.

In some embodiments of the invention, the subject is stratified by at least one demographic covariate. Such demographic covariates are known and recognizable by those of skill in the art and may include, without limitation, age, gender, race (e.g., White (Caucasian), Black (African American), Native American or Alaska Native, Asian, Native Hawaiian or Other Pacific Islander, Some Other Race), ethnicity (e.g., Hispanic or Latino), and county of residence. In preferred embodiments, the subject is stratified by at least one of age, race, ethnicity, gender, or any combination thereof. In some such embodiments, the subject is stratified into age brackets selected from ≤18 years old, 19 to 49 years old, 50 to 64 years old, and 65+ years old.

For example, in certain embodiments, the subject is Black, and the vaccine to be administered is at least one of a pneumococcal vaccine, a pneumococcal conjugate vaccine (e.g., PCV13), an RZV zoster vaccine, a diphtheria-pertussis-tetanus vaccine, or any combination thereof. In some such embodiments, the vaccine to be administered may be a pneumococcal vaccine and/or a pneumococcal conjugate vaccine (e.g., PCV13). Alternatively, the vaccine to be administered may be a pneumococcal conjugate vaccine (e.g., PCV13) or an RZV zoster vaccine. In other embodiments, wherein the subject is Black, the vaccine to be administered may be a pneumococcal vaccine or an RZV zoster vaccine. In certain embodiments, wherein the subject is white, the vaccine to be administered may be a geriatric flu vaccine or a polio vaccine. In further embodiments, wherein the subject is reported as Other (e.g., not any of White, Black, or Asian), the vaccine to be administered may be an RZV zoster vaccine. In some embodiments, the subject is less than 50 years old, preferably 19 to 49 years old. In some such embodiments, the vaccine to be administered may be an influenza vaccine.

In some embodiments of the invention disclosed herein, the subject is at risk of SARS-CoV-2 infection (e.g., at risk of exposure to or has been exposed to SARS-CoV-2 virus). In preferred embodiments, the subject is an essential or critical infrastructure worker. Such essential workers are known in the art and will be apparent to those of relevant skill. For example, and without limitation, such essential workers may include teachers, childcare providers, healthcare workers and caregivers, law enforcement officer, a public safety officer, first responders, and food and agriculture workers.

EXAMPLES

Example 1

Methods

Study Design

Disclosed herein is a retrospective study of patients who underwent polymerase chain reaction (PCR) testing for suspected SARS-CoV-2 infection at the Mayo Clinic and hospitals affiliated to the Mayo health system. The full dataset includes 152,548 patients who received PCR tests between Feb. 15, 2020 and Jul. 14, 2020. The study population was defined as 138,246 patients from this dataset who have at least one ICD code recorded in the past 5 years. This exclusion criteria is applied in order to restrict the analysis to the patients with available longitudinal health data. Among the study population, the COVIDpos cohort was defined as the patients with at least one positive PCR test result for SARS-CoV-2 infection, which includes 6,036 patients. Similarly, the COVIDneg cohort was defined as the patients with all negative PCR test results, which includes 132,210 patients.

For the study population of 138,246 patients, a number of clinical covariates were obtained from the Mayo Clinic electronic health record (EHR) database, including:
- demographics (age, gender, race, ethnicity, county of residence),
- diagnosis codes from the past 5 years (36,313 unique ICD codes), and
- immunization records from the past 5 years (68 unique vaccines; focus was on the 19 taken by at least 1000 patients over the past 5 years).

The Elixhauser Comorbidity Index was used to map the ICD codes from each patient from the past 5 years to a set of 17 medically relevant comorbidities.[16] In addition to the Mayo Clinic EHR database, the Corona Data Scraper online database was used to obtain incidence rates of COVID-19 at the county-level in the United States (Corona Data Scraper 2020). By linking the county of residence data from the EHR with the incidence rates of COVID-19 from Corona Data Scraper, county-level incidence rates of COVID-19 for 136,313 patients in the study population were obtained. County-level testing data for 100,433 patients in the study population from (i) Minnesota state government records and (ii) public county-level testing data scraped from other state/county websites were also obtained. In Table 1, the clinical characteristics of the study population and the average values for each of the clinical covariates in the study population. Notably, 92,673 (67%) of patients had at least 1 vaccine in the past 5 years relative to the PCR testing date.

TABLE 1

Summary of general characteristics of study population. County-level COVID incidence/testing and demographics, as well as overall vaccine prevalence and comorbidities for full study population based on available records.

| Characteristic | Proportion or mean over patients (n = 138,246) |
|---|---|
| County-level COVID-19 | |
| Incidence rate (+/−1 week from PCR date) | 0.0014 |
| Test positive rate (+/−1 week from PCR date) | 5.1% |
| Age | |
| 0-18 | 10,959 (7.9%) |
| 19-49 | 52,701 (38%) |
| 50-64 | 33,600 (24%) |
| 65+ | 40,986 (30%) |
| Gender | |
| Male | 61,309 (44%) |
| Female | 76,915 (56%) |
| Race | |
| White | 120,831 (87%) |
| Black | 5,533 (4%) |
| Asian | 3,297 (2.4%) |
| Other | 8,585 (6.2%) |
| Ethnicity | |
| Hispanic | 7,907 (5.7%) |
| Non-hispanic/unknown | 130,339 (94%) |
| Number of patients with at least 1 recorded vaccine | |
| Over past 1 year | 62213 (45%) |
| Over past 2 years | 75556 (55%) |
| Over past 5 years | 92673 (67%) |

TABLE 1-continued

Summary of general characteristics of study population. County-level COVID incidence/testing and demographics, as well as overall vaccine prevalence and comorbidities for full study population based on available records.

| Characteristic | Proportion or mean over patients (n = 138,246) |
| --- | --- |
| Elixhauser Comorbidities in the past 5 years | |
| Hypertension | 49,106 (36%) |
| Arrhythmias | 40,928 (30%) |
| Depression | 35,378 (26%) |
| Obesity | 34,575 (25%) |
| Pulmonary disease | 30,877 (22%) |
| Fluid and electrolyte disorders | 25,492 (18%) |
| Hypothyroidism | 20,769 (15%) |
| Peripheral vascular disorders | 19,484 (14%) |
| Valvular disease | 17,497 (13%) |
| Renal | 15,398 (11%) |
| Tumor (solid, without metastasis) | 13,916 (10%) |
| Liver disease | 13,158 (9.5%) |
| Congestive heart failure | 12,521 (9.1%) |
| Neurodegenerative disorders | 12,421 (9%) |
| Diabetes (complicated) | 12,102 (8.8%) |
| Anemia | 11,817 (8.5%) |
| Rheumatic diseases | 11,329 (8.2%) |
| Weight loss | 10,125 (7.3%) |
| Coagulopathy | 9,791 (7.1%) |
| Alcohol | 7,665 (5.5%) |
| Metastatic cancer | 7,401 (5.4%) |
| Drug abuse | 7,206 (5.2%) |
| Pulmonary hypertension | 6,951 (5%) |
| Diabetes (uncomplicated) | 6,855 (5%) |
| Peptic ulcer disease | 3,561 (2.6%) |
| Lymphoma | 3,234 (2.3%) |
| Blood loss | 2,485 (1.8%) |
| Paralysis | 1,794 (1.3%) |
| Psychoses | 1,447 (1%) |
| HIV/AIDS | 201 (0.15%) |

Given the clinical covariates, a series of statistical analyses were conducted to assess whether or not each of the 19 vaccines has a protective effect against COVID-19 at the 1 year, 2 years, and 5 year time horizons. In Table 2, we present the full names, common formulations, and counts for the 19 vaccines that we consider. For each vaccine and time horizon, the vaccinated cohort was defined as the set of patients in the study population who received the vaccine within the past time horizon. For example, the "2-year polio vaccinated cohort" was the set of patients who received the polio vaccine within the past two years. Similarly, for each vaccine and time horizon, the unvaccinated cohort was defined as the set of patients in the study population who did not receive the vaccine within the past time horizon. For example, the "5-year influenza unvaccinated cohort" was the set of patients who did not receive the influenza vaccine within the past five years.

TABLE 2

Summary of vaccines taken by 1000+ patients within 5 years prior to PCR testing. The 19 vaccines taken by 1000+ patients within 5 years prior to their PCR test date, along with most common formulations. Multiple individual formulations are merged into one "vaccine" in this analysis; the most common formulations/variants for each vaccine are shown; the shown formulations/variants generally account for the large majority of instances of the vaccine being administered. Note that some formulations (e.g. Pentacel) are counted for multiple vaccines.

| Vaccine name | Common Formulations | Number of patients taking in the past 5 years |
| --- | --- | --- |
| Diphtheria-Pertussis-Tetanus (DPT) | TDAP; TD preservative free | 49,147 |
| Geriatric Flu | High dose geriatric (65+ yrs) | 22,290 |
| Haemophilus Influenzae type B(HIB) | DTAP-IPV/HIB (PENTACEL) | 4,651 |
| Human Papillomavirus (HPV) | 9VHPV, 4VHPV | 6,266 |
| Hepatitis A/Hepatitis B (HepA-HepB) | HepA adult; HepB adult HepA pediatric/adolescent; HepB pediatric/adolescent | 15,772 |
| Influenza (live) | Influenza LAIV (Nasal) | 2,297 |
| Influenza general [Includes: Fluzone, Fluarix, Geriatric Flu, Pediatric Flu] | Quad (Fluzone/Fluarix); High dose geriatric (65+ yrs) | 78,043 |
| Measles-mumps-rubella (MMR) | MMR, MMRV | 6,836 |
| Meningococcal | MCV4, MENB | 7,147 |

TABLE 2-continued

Summary of vaccines taken by 1000+ patients within 5 years prior to PCR testing. The 19 vaccines taken by 1000+ patients within 5 years prior to their PCR test date, along with most common formulations. Multiple individual formulations are merged into one "vaccine" in this analysis; the most common formulations/variants for each vaccine are shown; the shown formulations/variants generally account for the large majority of instances of the vaccine being administered. Note that some formulations (e.g. Pentacel) are counted for multiple vaccines.

| Vaccine name | Common Formulations | Number of patients taking in the past 5 years |
| --- | --- | --- |
| Polio | DTAP-IPV/HIB (PENTACEL), IPV, DTAP-IPV | 5,862 |
| Pediatric Flu | IIV4 | 11,676 |
| Pneumococcal conjugate (PCV13) | PCV13 | 25,954 |
| Pneumococcal general [Includes: PCV7, PCV13, PPSV23] | PCV13, PPSV23, PCV7 | 35,031 |
| Pneumococcal polysaccharide (PPSV23) | PPSV23 | 17,422 |
| Rotavirus | RV5 (Rotateq) | 3,273 |
| RZV Zoster (Zostavax, Shingrix) | Zostavax, Shingrix | 17,630 |
| Tetanus | Td | 2,802 |
| Typhoid | TyVi, Ty21a | 2,393 |
| Varicella | VAR, MMRV | 5,783 |
| Pediatric Flu Vaccine | IIV4 | 11676 |
| Pneumococcal (PPSV23) |  | 17422 |
| Pneumococcal (any) | PCV13, PPSV23, PCV7 | 35031 |
| Pneumococcal conjugate (PCV13) |  | 25954 |
| ROTAVIRUS | RV5 (Rotateq) | 3273 |
| RZV Zoster (ZOSTAVAX, SHINGRIX) |  | 17630 |
| TETANUS | Td | 2802 |
| TYPHOID | TyVi, Ty21a | 2393 |
| VARICELLA | VAR, MMRV | 5783 |

The statistical methods that were used to compare the rates of COVID-19 between the vaccinated and unvaccinated cohorts for each of the (vaccine, time horizon) pairs are as follows. First, the propensity score matching analysis was defined to construct negative controls which have similar clinical characteristics to the vaccinated cohorts. Second, statistical tests were used to determine which of the (vaccine, time horizon) pairs have the most significant cross-protective effects against SARS-CoV-2 infection for the population level 1 year, 2 year, and 5 year time horizons; both overall and for particular demographic subgroups. Third, the covariate-level stratification analysis was used to identify which have the largest cross-protective effects for particular demographic subgroups. Finally, the sensitivity analyses used to evaluate the robustness of the statistical methods to potential biases from unobserved confounders or other factors that could impact the overall results from this observational study were defined.

Propensity Score Matching to Construct Negative Control Cohorts

Vaccinated cohorts with at least 1000 patients were filtered to, before running the propensity score matching step. For the overall statistical analysis, there were 15, 16, and 19 vaccines which met this threshold for the 1 year, 2 year, and 5 year time horizons, respectively.

For each vaccinated cohort with sufficient numbers of patients, a 1:1 propensity score matching was applied to construct a corresponding control cohort with similar clinical characteristics.[18] This is referred to as the "unvaccinated (matched)" cohort, which is a subset of the unvaccinated cohort. The following clinical covariates were considered in the propensity score matching step:

Demographics (Age, Gender, Race, Ethnicity)
County-level COVID-19 incidence rate: (Number of positive SARS-CoV-2 PCR tests in county)/(Total population of county) within +/−1 week of PCR testing date.
County-level COVID-19 test positive rate: (Number of positive SARS-CoV-2 PCR tests in county)/(Number of PCR tests in county) within +/−1 week of PCR testing date
Elixhauser comorbidities: Medical history derived from ICD diagnostic billing codes in the past 5 years relative to the PCR testing date. Includes indicators for the following conditions:
(1) congestive heart failure,
(2) cardiac arrhythmias,
(3) valvular disease,
(4) pulmonary circulation disorders,
(5) peripheral vascular disorders,
(6) hypertension,
(7) paralysis,
(8) neurodegenerative disorders,
(9) chronic pulmonary disease,
(10) diabetes,
(11) diabetes with complications,
(12) hypothyroidism,
(13) renal failure,
(14) liver disease,
(15) peptic ulcer disease (excluding bleeding),
(16) AIDS/HIV,
(17) lymphoma,
(18) metastatic cancer,
(19) solid tumor without metastasis,
(20) rheumatoid arthritis/collagen vascular diseases,
(21) coagulopathy,
(22) obesity,
(23) weight loss,

(24) fluid and electrolyte disorders,
(25) blood loss anemia,
(26) deficiency anemia,
(27) alcohol abuse,
(28) drug abuse,
(29) psychoses,
(30) depression.

Pregnancy: Whether or not the patient had a pregnancy-related ICD code recorded in the past 90 days relative to the PCR testing date.

Number of other vaccines: Count of the total number of unique vaccines taken by the patient in the past 5 years relative to the PCR testing date. The purpose of this control is to account for "healthy-user" effects (Shrank 2011), and also to account for the cross-protective effects from other vaccines A logistic regression model was fitted for each of the vaccinated cohorts to predict whether or not the patient received the vaccine as a function of these covariates. The logistic regression model was trained using the scikit-learn package in Python (Pedregosa et. al. 2011). The model-predicted probability of a patient receiving the vaccine as the propensity score for the patient was then used. Matching was done without replacement using greedy nearest-neighbor matching within calipers. Some patients could be dropped from the positive cohort in this procedure. The matching was performed on logits of this propensity score with caliper width 0.2*(pooled standard deviation of logits), as suggested by Austin.[20]

Statistical Assessment of the Cross Protective Effects of Existing Vaccines Against SARS-CoV-2 Infection for the Overall Study Population For each of the 64 cohorts, the extent of protective effect of the vaccine was assessed by computing relative risk of COVID+ rate between vaccinated and unvaccinated cohorts. A Fisher exact test was performed to compute p-values of protective (or anti-protective) effect. The FDR-controlling Benjamini-Hochberg adjustment was then applied on the p-values over all vaccines for each time horizon.[21]

Statistical Assessment of the Cross Protective Effects of Existing Vaccines Against SARS-CoV-2 Infection for Age and Race/ethnicity Stratified Subgroups The study population was stratified by both age and race/ethnicity simultaneously. Age was split into 4 age brackets: 0 to 18 years, 19 to 49 years old, 50 to 64 years old, and ≥65 years old (Lu et. al. 2013), and race/ethnicity was split into 4 strata: White, Black, Asian, and Hispanic (the Hispanic ethnicity stratum may not be disjoint from the others), giving 16 stratified subpopulations.

For each vaccine, at the 5-year time horizon, of the 16 corresponding stratified vaccinated cohorts; those stratified cohorts with 100+ patients were filtered to. This left 59 (vaccine, age subgroup) and 80 (vaccine, race subgroup) pairs which met this threshold for the 1 year, 2 year, and 5 year time horizons, respectively. The propensity score matching procedure was performed on each of these stratified vaccinated cohorts. The negative controls were taken from the unvaccinated portion of the corresponding stratified subpopulation. Matching was done on the same covariates as in the overall analysis (apart from the Race/Ethnicity covariates). Relative risk and Fisher exact p-values were computed for each stratified vaccinated cohort.

Negative Control for Matching Procedure

To assess the validity of the overall statistical procedure, the procedure was applied on a "negative control" for vaccines. For a plausible negative control "having had a mammogram" was chosen; similar "healthy-user" effects were expected to generally apply for both, and any protective effect should not be observed for SARS-CoV-2 infection. The relative risk and Fisher exact p-values were calculated before and after propensity matching, shown in Table 3.

TABLE 3

Summary of SARS-CoV-2 rates for patients who received vs did not receive negative control treatments (mammograms, colon screens). SARS-CoV-2 positive rates, relative risks, and associated Fisher exact p-values for patients who received vs did not receive mammogram & colon screen over 1 year, 2 years, and 5 years prior to PCR test; the numbers are shown before and after propensity score matching. Unmatched numbers are shown below corresponding matched numbers.

| Control | Time horizon, matching strategy | Total treated | Treated $COVID_{pos}$ rate | Untreated $COVID_{pos}$ rate | Relative risk | Fisher exact p-value |
|---|---|---|---|---|---|---|
| Mammogram | 1-year, matched | 12343 | 2.1% | 2.5% | 0.85 | 0.05 |
| | 1-year, unmatched | 12347 | 2.2% | 4.5% | 0.49 | 1.3E−45 |
| | 2-year, matched | 15855 | 2.4% | 2.5% | 0.94 | 0.41 |
| | 2-year, unmatched | 18268 | 2.4% | 4.5% | 0.53 | 8.1E−54 |
| | 5-year, matched | 18484 | 2.7% | 2.7% | 0.99 | 0.95 |
| | 5-year, unmatched | 24232 | 2.5% | 4.7% | 0.53 | 6.6E−60 |
| Colon screen | 1-year, matched | 6040 | 2.2% | 2.3% | 0.94 | 0.62 |
| | 1-year, unmatched | 6040 | 2.1% | 4.6% | 0.46 | 8.2E−21 |
| | 2-year, matched | 11328 | 2.4% | 2.6% | 0.93 | 0.40 |
| | 2-year, unmatched | 11329 | 2.3% | 4.7% | 0.50 | 6.9E−54 |
| | 5-year, matched | 21593 | 2.5% | 2.5% | 1.0 | 0.98 |
| | 5-year, unmatched | 21595 | 2.5% | 4.8% | 0.53 | 9.5E−56 |

Example 2

DPT, Pneumococcal, HIB, Polio, and Geriatric Flu Vaccines Consistently Show Associations with Lower Rates of SARS-CoV-2 Infection Across 1, 2, and 5 Year Time Horizons In FIG. 1, the relative SARS-CoV-2 infection rates for subsets of the study population with particular clinical covariates is presented. Rates of SARS-CoV-2 infection appeared to be much higher in Black, Asian, and Hispanic racial and ethnic subgroups compared to the overall study population. In addition, the rates of SARS-CoV-2 infection are higher in patients with pre-existing conditions (e.g. hypertension, diabetes, obesity) due to the fact that these patients receive higher rates of PCR tests.

The results of the propensity score matching for the 1 year, 2 year, and 5 year time horizons are presented in Tables 4 to 6, respectively. Across all time horizons, Diphtheria-Pertussis-Tetanus (DPT), Pneumococcal (general), Haemophilus Influenzae type B (HIB), and Geriatric Flu vaccines showed consistent lower rates of SARS-CoV-2 infection.

TABLE 4

Summary of SARS-CoV-2 rates for vaccinated and unvaccinated (matched) cohorts for vaccines taken by at least 1,000 patients within 1 year prior to PCR testing.

| Vaccine | Total matched pairs | Vaccinated $COVID_{pos}$ count (rate), matched | Unvaccinated $COVID_{pos}$ count (rate), matched | Relative risk (95% CI) | BH-adjusted p-value |
|---|---|---|---|---|---|
| HIB | 2183 | 46 (2.11%) | 79 (3.62%) | 0.58 (0.41, 0.84) | 0.02 |
| Geriatric Flu Vaccine (65+ Yrs) | 10678 | 163 (1.53%) | 219 (2.05%) | 0.74 (0.61, 0.91) | 0.02 |
| Diphtheria (with P/T) | 12605 | 431 (3.42%) | 516 (4.09%) | 0.84 (0.74, 0.95) | 0.02 |
| MMR | 2134 | 59 (2.76%) | 93 (4.36%) | 0.63 (0.46, 0.88) | 0.02 |
| Pneumococcal conjugate (PCV13) | 5009 | 105 (2.1%) | 142 (2.83%) | 0.74 (0.58, 0.95) | 0.06 |
| Polio | 1788 | 53 (2.96%) | 79 (4.42%) | 0.67 (0.48, 0.95) | 0.07 |
| Pneumococcal (general) | 9827 | 215 (2.19%) | 259 (2.64%) | 0.83 (0.69, 0.99) | 0.09 |
| HepA-HepB | 6300 | 195 (3.1%) | 236 (3.75%) | 0.83 (0.69, 1.00) | 0.09 |
| VARICELLA | 1782 | 50 (2.81%) | 71 (3.98%) | 0.70 (0.50, 1.01) | 0.11 |
| Pneumococcal (PPSV23) | 5200 | 115 (2.21%) | 142 (2.73%) | 0.81 (0.64, 1.03) | 0.15 |
| Meningococcal | 1643 | 100 (6.09%) | 82 (4.99%) | 1.22 (0.92, 1.62) | 0.27 |
| RZV Zoster (ZOSTAVAX, SHINGRIX) | 10197 | 215 (2.11%) | 242 (2.37%) | 0.89 (0.74, 1.07) | 0.27 |
| Influenza (general) | 17902 | 642 (3.59%) | 624 (3.49%) | 1.03 (0.92, 1.15) | 0.72 |
| HPV | 1584 | 93 (5.87%) | 93 (5.87%) | 1 (0.76, 1.32) | 1 |

* Cohorts indicating significant protective effects (adjusted p-value < 0.05) are shown in bold; cohorts indicating significant anti-protective effects are shown in italics. The columns are
(1) Vaccine;
(2) Total matched vaccinated/unvaccinated pairs -- the number of pairs from the propensity matching procedure, i.e. the sample size of both vaccinated and unvaccinated cohorts after matching,
(3) Vaccinated COVID+ count (rate), matched - the number (& proportion) of COVID+ cases among the vaccinated members of those pairs,
(4) unvaccinated COVID+ count (rate), matched - the number (&proportion) of COVID+ cases among the unvaccinated members of those pairs,
(5) Relative risk - vaccinated COVID+ rate divided by unvaccinated COVID+ rate,
(6) BH-adjustedp-value - Benjamini-Hochberg-adjusted Fisher exact test p-values, See Tables 4 and 5 for the equivalent results for the 2 year and 5 year time horizons for vaccination, respectively.

TABLE 5

Summary of SARS-CoV-2 rates for vaccinated and unvaccinated matched cohorts for vaccines taken by at least 1,000 patients within 2 years prior to PCR testing.

| Vaccine | Total matched pairs | Vaccinated COVID+ count (rate), matched | Unvaccinated COVID+ count (rate), matched | Relative risk | BH-adjusted p-value |
|---|---|---|---|---|---|
| HepA-HepB | 8375 | 263 (3.14%) | 344 (4.11%) | 0.76 (0.65, 0.90) | 0.01 |
| HIB | 2250 | 56 (2.49%) | 94 (4.18%) | 0.60 (0.43, 0.83) | 0.02 |
| Meningococcal | 3187 | 227 (7.12%) | 172 (5.4%) | 1.32 (1.09, 1.60) | 0.03 |
| Pneumococcal (general) | 16009 | 373 (2.33%) | 450 (2.81%) | 0.83 (0.72, 0.95) | 0.03 |
| Diphtheria (with P/T) | 21032 | 788 (3.75%) | 886 (4.21%) | 0.89 (0.81, 0.98) | 0.05 |
| Polio | 1633 | 63 (3.86%) | 93 (5.7%) | 0.68 (0.50, 0.93) | 0.05 |
| Pneumococcal conjugate (PCV13) | 8596 | 188 (2.19%) | 230 (2.68%) | 0.82 (0.68, 0.99) | 0.1 |
| Geriatric Flu Vaccine (65+ Yrs) | 10644 | 189 (1.78%) | 225 (2.11%) | 0.84 (0.69, 1.02) | 0.16 |

TABLE 5-continued

Summary of SARS-CoV-2 rates for vaccinated and unvaccinated matched cohorts for vaccines taken by at least 1,000 patients within 2 years prior to PCR testing.

| Vaccine | Total matched pairs | Vaccinated COVID+ count (rate), matched | Unvaccinated COVID+ count (rate), matched | Relative risk | BH-adjusted p-value |
|---|---|---|---|---|---|
| Typhoid | 1059 | 72 (6.8%) | 53 (5%) | 1.36 (0.96, 1.91) | 0.17 |
| RZV Zoster (ZOSTAVAX, SHINGRIX) | 14787 | 296 (2%) | 335 (2.27%) | 0.88 (0.76, 1.03) | 0.2 |
| MMR | 2872 | 103 (3.59%) | 124 (4.32%) | 0.83 (0.64, 1.07) | 0.26 |
| Pneumococcal (PPSV23) | 9320 | 213 (2.29%) | 239 (2.56%) | 0.89 (0.74, 1.07) | 0.31 |
| HPV | 2733 | 179 (6.55%) | 199 (7.28%) | 0.90 (0.74, 1.09) | 0.38 |
| Influenza (general) | 22816 | 880 (3.86%) | 903 (3.96%) | 0.97 (0.89, 1.07) | 0.68 |
| VARICELLA | 2285 | 86 (3.76%) | 86 (3.76%) | 1 (0.75, 1.34) | 1 |
| ROTAVIRUS | 500 | 12 (2.4%) | 11 (2.2%) | 1.09 (0.49, 2.40) | 1 |

TABLE 6

Summary of SARS-CoV-2 rates for vaccinated and unvaccinated matched cohorts for vaccines taken by at least 1,000 patients within 5 years prior to PCR testing

| Vaccine | Total matched pairs | Vaccinated COVID+ count (rate), matched | Non-vaccinated COVID+ count (rate), matched | Relative risk (95% CI) | BH-adjusted p-value |
|---|---|---|---|---|---|
| Polio | 2029 | 101 (4.98%) | 166 (8.18%) | 0.61 (0.48, 0.77) | 7.2E−04 |
| Meningococcal | 7147 | 556 (7.78%) | 435 (6.09%) | 1.28 (1.13, 1.44) | 7.2E−04 |
| Typhoid | 2392 | 150 (6.27%) | 95 (3.97%) | 1.58 (1.23, 2.02) | 2.4E−03 |
| Pneumococcal (general) | 18034 | 477 (2.65%) | 584 (3.24%) | 0.82 (0.73, 0.92) | 4.5E−03 |
| Geriatric Flu Vaccine (65+ Yrs) | 12864 | 244 (1.9%) | 319 (2.48%) | 0.76 (0.65, 0.90) | 6.0E−03 |
| Pneumococcal conjugate (PCV13) | 16612 | 375 (2.26%) | 463 (2.79%) | 0.81 (0.71, 0.93) | 7.3E−03 |
| VARICELLA | 3523 | 191 (5.42%) | 249 (7.07%) | 0.77 (0.64, 0.92) | 0.01 |
| RZV Zoster (ZOSTAVAX, SHINGRIX) | 17611 | 360 (2.04%) | 435 (2.47%) | 0.83 (0.72, 0.95) | 0.02 |
| Diphtheria (with P/T) | 42147 | 1681 (3.99%) | 1822 (4.32%) | 0.92 (0.86, 0.98) | 0.03 |
| Influenza (general) | 26682 | 1216 (4.56%) | 1106 (4.15%) | 1.10 (1.02, 1.19) | 0.04 |
| HPV | 6266 | 495 (7.9%) | 438 (6.99%) | 1.13 (1.00, 1.28) | 0.1 |
| HIB | 1577 | 51 (3.23%) | 72 (4.57%) | 0.71 (0.50, 1.01) | 0.1 |
| MMR | 4574 | 213 (4.66%) | 251 (5.49%) | 0.85 (0.71, 1.01) | 0.11 |
| TETANUS | 2800 | 88 (3.14%) | 76 (2.71%) | 1.16 (0.86, 1.56) | 0.52 |
| HepA-HepB | 12158 | 517 (4.25%) | 540 (4.44%) | 0.96 (0.85, 1.08) | 0.62 |
| Pneumococcal (PPSV23) | 17380 | 417 (2.4%) | 435 (2.5%) | 0.96 (0.84, 1.09) | 0.66 |
| ROTAVIRUS | 580 | 18 (3.1%) | 22 (3.79%) | 0.82 (0.45, 1.50) | 0.7 |
| Influenza (Live) | 2297 | 110 (4.79%) | 117 (5.09%) | 0.94 (0.73, 1.21) | 0.72 |
| Pediatric Flu Vaccine | 11604 | 426 (3.67%) | 426 (3.67%) | 1.00 (0.88, 1.14) | 1 |

Figure 2:
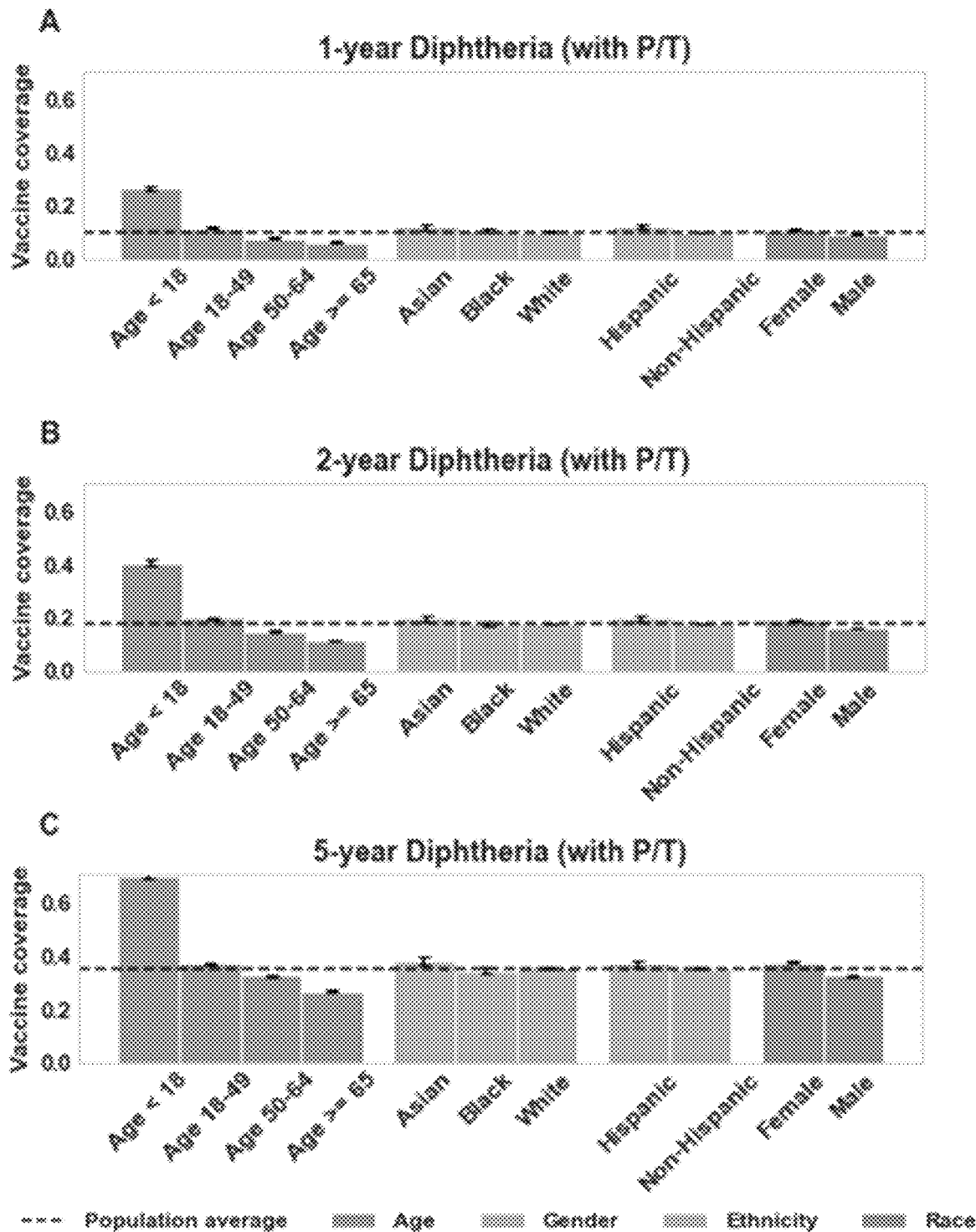
FIG. 2 shows vaccination coverage rates among patients stratified by different demographic factors (Age, Race, Ethnicity and Gender), along with 95% confidence intervals and baseline population vaccination rate.
Figure 2:
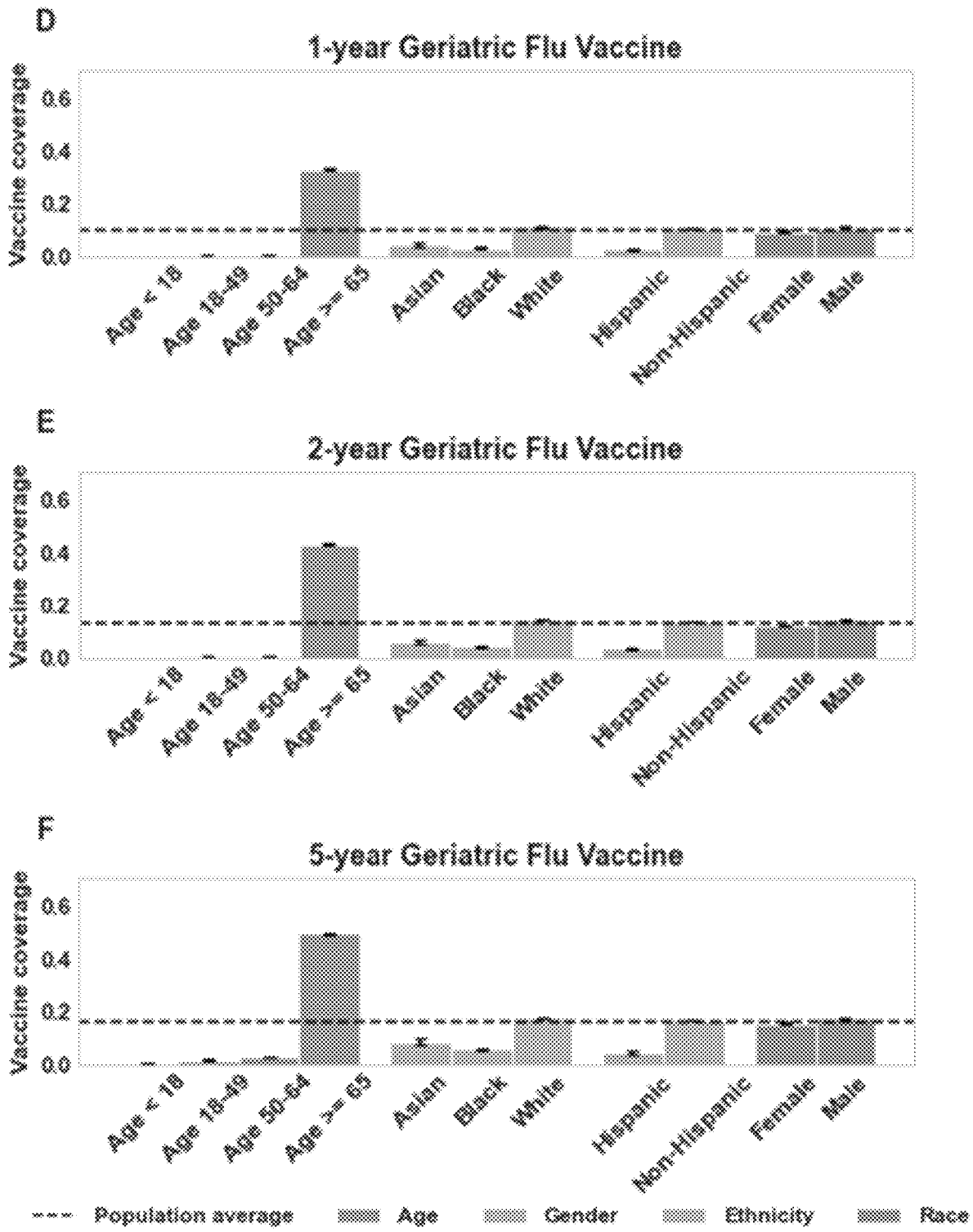
Figure 2:
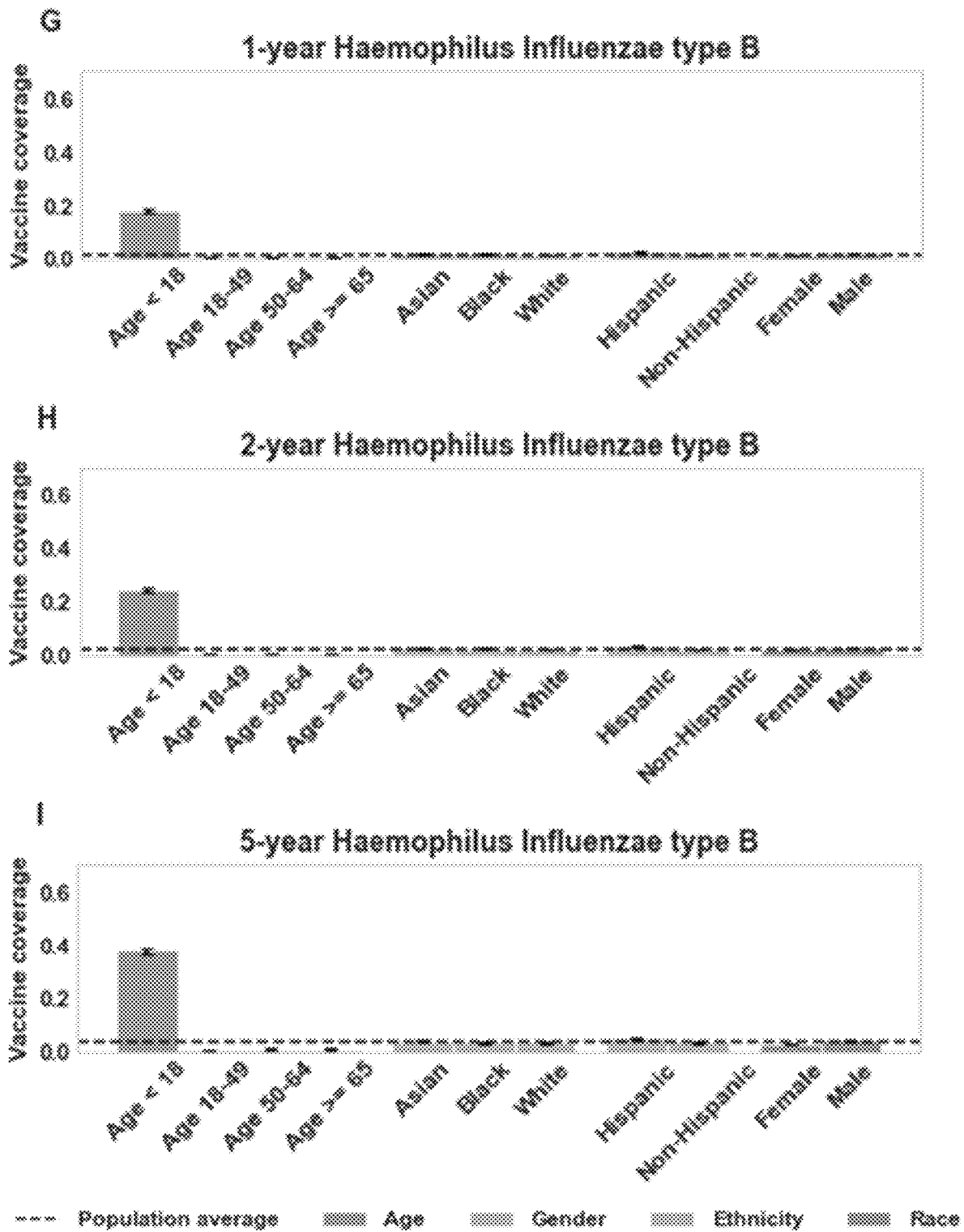
Figure 2:
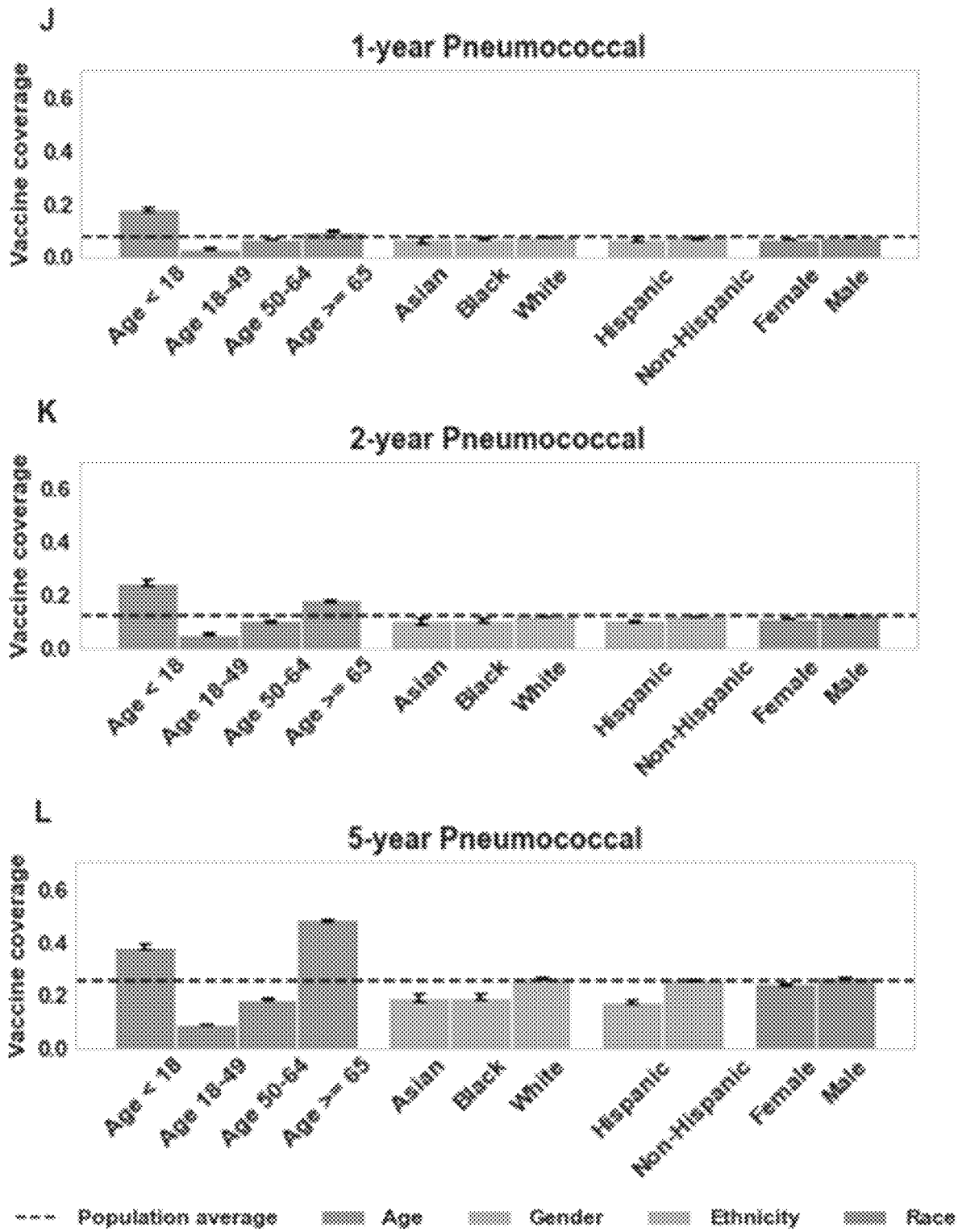
Figure 2:
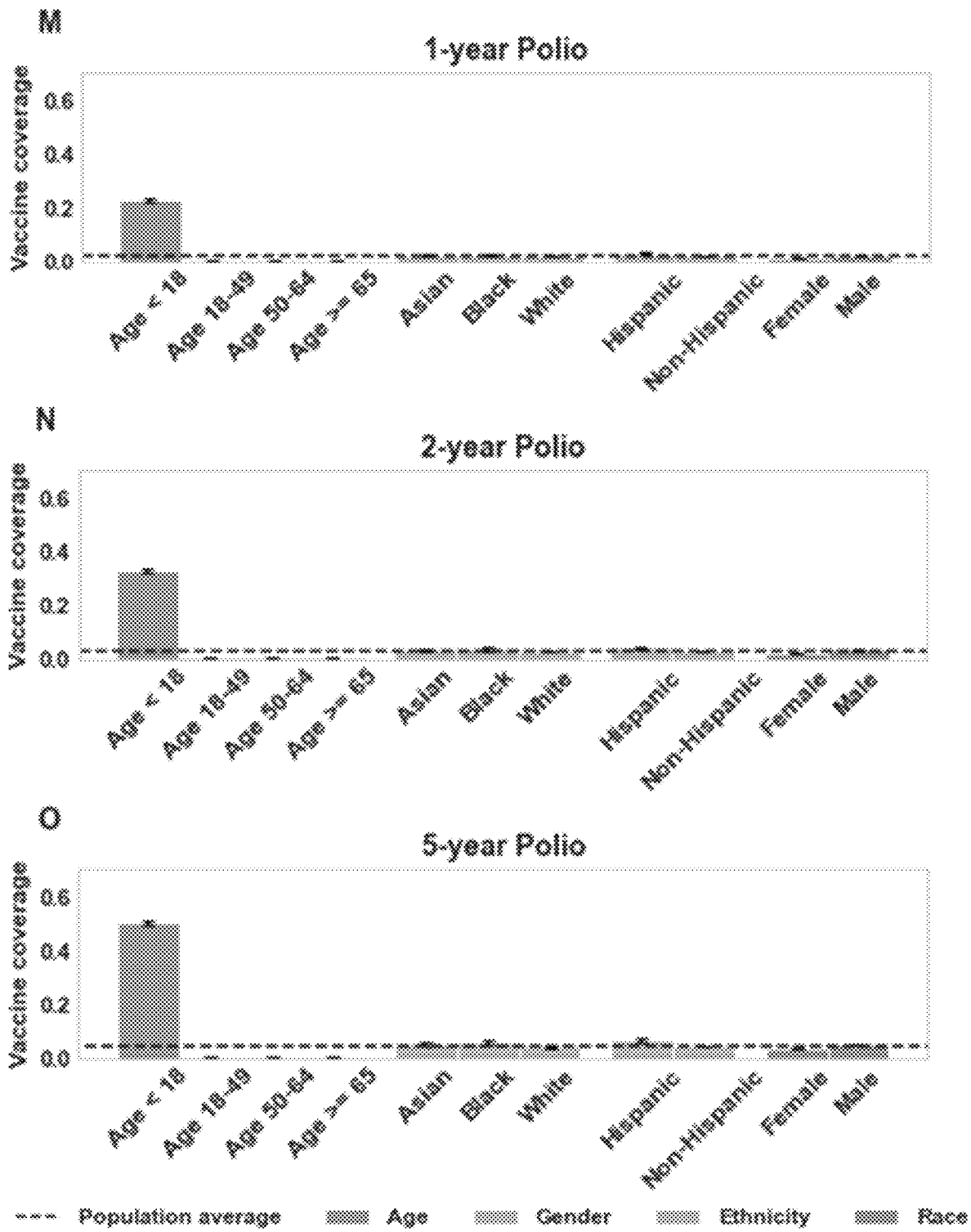

In Tables 7 to 11, the clinical characteristics for the vaccinated, unvaccinated, and matched cohorts for each of these vaccines at the 5 year time horizon are shown. In FIG. 2, the vaccination coverage rates for each of these vaccines in the study population are shown as well.

TABLE 7

Covariates for the DPT vaccine over the 5-year time horizon horizon in vaccinated (matched), unvaccinated (matched), vaccinated (original) and unvaccinated (original) cohorts.

| Covariate | Mean/proportion among vaccinated (n = 42147) | Mean/proportion among unvaccinated (n = 42147) | Unmatched mean/proportion among vaccinated (n = 49147) | Unmatched mean/proportion among unvaccinated (n = 89099) |
|---|---|---|---|---|
| COVID+ rate | 3.99% | 4.32% | 3.82% | 4.67% |
| County incidence | 0.14% | 0.14% | 0.14% | 0.15% |
| County PCR test positive rate | 4.86% | 4.88% | 4.79% | 5.37% |

TABLE 7-continued

Covariates for the DPT vaccine over the 5-year time horizon horizon in vaccinated (matched), unvaccinated (matched), vaccinated (original) and unvaccinated (original) cohorts.

| Covariate | Mean/proportion among vaccinated (n = 42147) | Mean/proportion among unvaccinated (n = 42147) | Unmatched mean/proportion among vaccinated (n = 49147) | Unmatched mean/proportion among unvaccinated (n = 89099) |
|---|---|---|---|---|
| Age | 48.6 | 48.9 | 44.3 | 52.9 |
| Gender - Male | 17324 (41.1%) | 17905 (42.5%) | 20049 (40.8%) | 41260 (46.3%) |
| Race - White | 37240 (88.4%) | 37660 (89.4%) | 43266 (88%) | 77565 (87.1%) |
| Race - Black | 1624 (3.85%) | 1467 (3.48%) | 1928 (3.92%) | 3605 (4.05%) |
| Race - Asian | 1052 (2.5%) | 1018 (2.42%) | 1257 (2.56%) | 2040 (2.29%) |
| Ethnicity - Hispanic | 2361 (5.6%) | 2308 (5.48%) | 2943 (5.99%) | 4964 (5.57%) |
| Elixhauser - Hypertension | 15594 (37%) | 16029 (38%) | 16433 (33.4%) | 32673 (36.7%) |
| Elixhauser - Pulmonary | 11015 (26.1%) | 11184 (26.5%) | 12414 (25.3%) | 18463 (20.7%) |
| Elixhauser - Diabetes mellitus | 1976 (4.69%) | 1923 (4.56%) | 2087 (4.25%) | 4768 (5.35%) |
| Elixhauser - Diabetes mellitus (complications) | 4167 (9.89%) | 4293 (10.2%) | 4382 (8.92%) | 7720 (8.66%) |
| Elixhauser - Coagulopathy | 3184 (7.55%) | 3145 (7.46%) | 3598 (7.32%) | 6193 (6.95%) |
| Elixhauser - Obesity | 12706 (30.1%) | 12893 (30.6%) | 14071 (28.6%) | 20504 (23%) |
| Pregnancy - 90 days preceding | 0.02 | 0.01 | 0.05 | 0.01 |
| # unique other vaccines taken over preceding 5 y | 2.88 | 2.7 | 3.47 | 1.48 |
| Propensity score | 0.56 | 0.54 | 0.61 | 0.39 |

TABLE 8

Covariates for the 5-year pneumococcal (general) vaccinated (matched), unvaccinated (matched), vaccinated (original) and unvaccinated (original) cohorts.

| Covariate | Mean/proportion among vaccinated (n = 18034) | Mean/proportion among unvaccinated (n = 18034) | Unmatched mean/proportion among vaccinated (n = 35031) | Unmatched mean/proportion among unvaccinated (n = 103215) |
|---|---|---|---|---|
| COVID+ rate | 2.65% | 3.24% | 2.26% | 5.08% |
| County incidence | 0.13% | 0.13% | 0.12% | 0.15% |
| County PCR test positive rate | 4.70% | 4.72% | 4.61% | 5.33% |
| Age | 57 | 55.4 | 58.4 | 46.9 |
| Gender - Male | 8167 (45.3%) | 7785 (43.2%) | 16406 (46.8%) | 44903 (43.5%) |
| Race - White | 16334 (90.6%) | 16299 (90.4%) | 32072 (91.6%) | 88759 (86%) |
| Race - Black | 601 (3.33%) | 634 (3.52%) | 1068 (3.05%) | 4465 (4.33%) |
| Race - Asian | 363 (2.01%) | 350 (1.94%) | 627 (1.79%) | 2670 (2.59%) |
| Ethnicity - Hispanic | 777 (4.31%) | 747 (4.14%) | 1373 (3.92%) | 6534 (6.33%) |
| Elixhauser - Hypertension | 9401 (52.1%) | 9305 (51.6%) | 20684 (59%) | 28422 (27.5%) |
| Elixhauser - Pulmonary | 5596 (31%) | 6154 (34.1%) | 12374 (35.3%) | 18503 (17.9%) |
| Elixhauser - Diabetes mellitus | 1257 (6.97%) | 1206 (6.69%) | 2667 (7.61%) | 4188 (4.06%) |
| Elixhauser - Diabetes mellitus (complications) | 2466 (13.7%) | 2638 (14.6%) | 6174 (17.6%) | 5928 (5.74%) |
| Elixhauser - Coagulopathy | 1791 (9.93%) | 1773 (9.83%) | 4522 (12.9%) | 5269 (5.1%) |
| Elixhauser - Obesity | 5927 (32.9%) | 6318 (35%) | 12094 (34.5%) | 22481 (21.8%) |
| Pregnancy - 90 days preceding | 142 (0.787%) | 171 (0.948%) | 151 (0.431%) | 2640 (2.56%) |
| # unique other vaccines taken over preceding 5 y | 3.7 | 3.56 | 4.8 | 1.43 |
| Propensity score | 0.65 | 0.63 | 0.79 | 0.21 |

TABLE 9

Covariates for the 5-year HIB vaccinated (matched), unvaccinated (matched), vaccinated (original) and unvaccinated (original) cohorts.

| Covariate | Mean/proportion among vaccinated (n = 1577) | Mean/proportion among unvaccinated (n = 1577) | Unmatched mean/proportion among vaccinated (n = 4651) | Unmatched mean/proportion among unvaccinated (n = 133595) |
|---|---|---|---|---|
| COVID+ rate | 3.23% | 4.57% | 2.56% | 4.43% |
| County incidence | 0.13% | 0.13% | 0.11% | 0.14% |
| County PCR test positive rate | 4.78% | 4.78% | 4.55% | 5.16% |
| Age | 25.2 | 33.3 | 12.4 | 51.1 |
| Gender - Male | 750 (47.6%) | 873 (55.4%) | 2452 (52.7%) | 58857 (44.1%) |
| Race - White | 1282 (81.3%) | 1296 (82.2%) | 3976 (85.5%) | 116855 (87.5%) |
| Race - Black | 87 (5.52%) | 113 (7.17%) | 177 (3.81%) | 5356 (4.01%) |
| Race - Asian | 63 (3.99%) | 38 (2.41%) | 129 (2.77%) | 3168 (2.37%) |
| Ethnicity - Hispanic | 149 (9.45%) | 112 (7.1%) | 397 (8.54%) | 7510 (5.62%) |
| Elixhauser - Hypertension | 390 (24.7%) | 476 (30.2%) | 522 (11.2%) | 48584 (36.4%) |
| Elixhauser - Pulmonary | 327 (20.7%) | 364 (23.1%) | 661 (14.2%) | 30216 (22.6%) |
| Elixhauser - Diabetes mellitus | 50 (3.17%) | 51 (3.23%) | 61 (1.31%) | 6794 (5.09%) |
| Elixhauser - Diabetes mellitus (complications) | 128 (8.12%) | 204 (12.9%) | 153 (3.29%) | 11949 (8.94%) |
| Elixhauser - Coagulopathy | 218 (13.8%) | 432 (27.4%) | 424 (9.12%) | 9367 (7.01%) |
| Elixhauser - Obesity | 248 (15.7%) | 241 (15.3%) | 315 (6.77%) | 34260 (25.6%) |
| Pregnancy - 90 days preceding | 2 (0.127%) | 8 (0.507%) | 4 (0.086%) | 2787 (2.09%) |
| # unique other vaccines taken over preceding 5 y | 6.83 | 6.49 | 8.4 | 2.3 |
| Propensity score | 0.72 | 0.71 | 0.87 | 0.13 |

TABLE 10

Covariates for the 5-year Polio vaccinated (matched), unvaccinated (matched), vaccinated (original) and unvaccinated (original) cohorts.

| Covariate | Mean/proportion among vaccinated (n = 2029) | Mean/proportion among unvaccinated (n = 2029) | Unmatched mean/proportion among vaccinated (n = 5862) | Unmatched mean/proportion among unvaccinated (n = 132384) |
|---|---|---|---|---|
| COVID+ rate | 4.98% | 8.18% | 3.53% | 4.40% |
| County incidence | 0.15% | 0.16% | 0.12% | 0.14% |
| County PCR test positive rate | 5.03% | 5.24% | 4.65% | 5.17% |
| Age | 21.2 | 24.9 | 9.9 | 51.6 |
| Gender - Male | 979 (48.3%) | 1125 (55.4%) | 3046 (52%) | 58263 (44%) |
| Race - White | 1620 (79.8%) | 1439 (70.9%) | 4822 (82.3%) | 116009 (87.6%) |
| Race - Black | 146 (7.2%) | 268 (13.2%) | 333 (5.68%) | 5200 (3.93%) |
| Race - Asian | 63 (3.1%) | 100 (4.93%) | 174 (2.97%) | 3123 (2.36%) |
| Ethnicity - Hispanic | 196 (9.66%) | 170 (8.38%) | 538 (9.18%) | 7369 (5.57%) |
| Elixhauser - Hypertension | 292 (14.4%) | 198 (9.76%) | 367 (6.26%) | 48739 (36.8%) |
| Elixhauser - Pulmonary | 401 (19.8%) | 435 (21.4%) | 823 (14%) | 30054 (22.7%) |
| Elixhauser - Diabetes mellitus | 41 (2.02%) | 30 (1.48%) | 52 (0.887%) | 6803 (5.14%) |
| Elixhauser - Diabetes mellitus (complications) | 82 (4.04%) | 66 (3.25%) | 96 (1.64%) | 12006 (9.07%) |
| Elixhauser - Coagulopathy | 189 (9.31%) | 238 (11.7%) | 348 (5.94%) | 9443 (7.13%) |
| Elixhauser - Obesity | 267 (13.2%) | 171 (8.43%) | 351 (5.99%) | 34224 (25.9%) |
| Pregnancy - 90 days preceding | 16 (0.789%) | 20 (0.986%) | 18 (0.307%) | 2773 (2.09%) |
| # unique other vaccines taken over preceding 5 y | 5.46 | 5.4 | 7.63 | 2.27 |
| Propensity score | 0.7 | 0.69 | 0.87 | 0.13 |

TABLE 11

Covariates for the 5-year Geriatric Flu vaccinated (matched), unvaccinated (matched), vaccinated (original) and unvaccinated (original) cohorts.

| Covariate | Mean/proportion among vaccinated (n = 12864) | Mean/proportion among unvaccinated (n = 12864) | Unmatched mean/proportion among vaccinated (n = 22290) | Unmatched mean/proportion among unvaccinated (n = 115956) |
|---|---|---|---|---|
| COVID+ rate | 1.90% | 2.48% | 1.69% | 4.88% |
| County incidence | 0.13% | 0.12% | 0.12% | 0.15% |
| County PCR test positive rate | 4.75% | 4.67% | 4.59% | 5.25% |
| Age | 70.7 | 67.4 | 73.6 | 45.3 |
| Gender - Male | 6240 (48.5%) | 5835 (45.4%) | 10493 (47.1%) | 50816 (43.8%) |
| Race - White | 12141 (94.4%) | 11968 (93%) | 21293 (95.5%) | 99538 (85.8%) |
| Race - Black | 227 (1.76%) | 351 (2.73%) | 312 (1.4%) | 5221 (4.5%) |
| Race - Asian | 188 (1.46%) | 198 (1.54%) | 280 (1.26%) | 3017 (2.6%) |
| Ethnicity - Hispanic | 277 (2.15%) | 303 (2.36%) | 348 (1.56%) | 7559 (6.52%) |
| Elixhauser - Hypertension | 8838 (68.7%) | 8570 (66.6%) | 16657 (74.7%) | 32449 (28%) |
| Elixhauser - Pulmonary | 4281 (33.3%) | 4364 (33.9%) | 8042 (36.1%) | 22835 (19.7%) |
| Elixhauser - Diabetes mellitus | 1031 (8.01%) | 1020 (7.93%) | 1763 (7.91%) | 5092 (4.39%) |
| Elixhauser - Diabetes mellitus (complications) | 2375 (18.5%) | 2417 (18.8%) | 4596 (20.6%) | 7506 (6.47%) |

The relative risk of SARS-CoV-2 infection for patients who have taken the Diphtheria-Pertussis-Tetanus (DPT) vaccine is 0.84 at the 1 year time horizon (95% CI: (0.74, 0.95), p-value: 0.02), 0.89 at the 2 year time horizon (95% CI: (0.81, 0.98), p-value: 0.05), and 0.92 at the 5 year time horizon (95% CI: (0.86, 0.98), p-value: 0.0403). Here, we see that the protective effectrelative risk gradually wanesincreases as the time horizon increases. In the study population, the DPT vaccine is most commonly administered to younger patients. In particular, the 5 year DPT vaccination rates are 70%, 37%, 33%, and 27% for the <18, (total: 10,128 patients), 18-49, (total: 53,532 patients), 50-64, (total: 33,600 patients), and 65+ age brackets (total: 40,986 patients) (see Table 1, FIG. 2C).

Additional vaccines with consistent cross-protective effects that are commonly administered to younger patients and associated with lower rates of SARS-CoV-2 infection include Polio and HIB. For the <18, 18-49, 50-64, and 65+ age brackets, the 5 year Polio vaccination rates are 50%, 0.6%, 0.6%, and 0.6% (see FIG. 2O) and the 5 year HIB vaccination rates are 38%, 0.3%, 0.8%, and 0.9% (see FIG. 2I). The relative risk values for the Polio vaccinated cohort are 0.67 (95% CI: (0.48, 0.95), p-value: 0.07), 0.68 (95% CI: (0.50, 0.93), p-value: 0.05), 0.61 (95% CI: (0.48, 0.77), p-value: 7.6e2e-4) for the 1, 2, and 5 year time horizons, respectively. Similarly, the relative risk values for HIB are 0.58 (95% CI: (0.41, 0.84), p-value: 0.02), 0.60 (95% CI: (0.43, 0.83), p-value: 0.02), 0.71 (95% CI: (0.50, 1.01), p-value: 0.111) for the 1, 2, and 5 year time horizons, respectively.

The other vaccines that show consistent cross-protective effects across time horizons are Pneumococcal (general), PCV13, and Geriatric Flu. All of these vaccines are administered at higher rates to White and non-Hispanic patients (see FIG. 2). The observed relative risks were 0.83 (95% CI: (0.69, 0.99), p-value: 0.09), 0.83 (95% CI: (0.72, 0.95), p-value: 0.03), and 0.82 (95% CI: (0.73, 0.92), p-value: 4.7e5e-3) for the Pneumococcal (general) vaccine, 0.74 (95% CI: (0.58, 0.95), p-value: 0.06), 0.82 (95% CI: (0.68, 0.99), p-value: 0.10), and 0.81 (95% CI: (0.71, 0.93), p-value: 7.7e3e-3) for the PCV13 vaccine, and 0.74 (95% CI: (0.61, 0.91), p-value: 0.02), 0.84 (95% CI: (0.69, 1.02), p-value: 0.1816), and 0.76 (95% CI: (0.65, 0.90), p-value: 6.4e0e-3) for the Geriatric Flu vaccine at the 1, 2, and 5 year time horizons, respectively.

Example 3

Significantly Reduced SARS-CoV-2 Rates Over Particular Time Periods for MMR (1 year), HepA-HepB (2 year), Varicella (5 year), and RZV Zoster (5 year) Vaccines Some vaccines were significantly associated with decreased rates of SARS-CoV-2 infection for particular time horizons only. For the 1 year time horizon, measles-mumps-rubella (MMR) vaccine has a relative risk of 0.63 (p-value: 0.02). For the 2 year time horizon, Hepatitis A/Hepatitis B (HepA-HepB) vaccine has a relative risk of 0.76 (p-value: 0.02). In contrast, at the 5 year time horizon, the relative risks for MMR and HepA-HepB are 0.85 and 0.96, respectively. This suggests that the protective effect from the MMR and HepA-HepB vaccines may wear off over time.

On the other hand, significant cross-protective effects for the Varicella and RZV Zoster vaccines at the 5 year time horizon were observed, but not for the shorter time horizons. Notably, the relative risks at the 5 year time horizon are 0.77 for Varicella (p-value: 0.01) and 0.83 for RZV Zoster (p-value: 0.02). For the Varicella vaccine, the lack of a significant protective effect at the shorter time horizons may be due to smaller sample sizes of the vaccinated cohort. For the RZV Zoster vaccine, although the sample sizes are larger, the protective effect is much smaller, so this vaccine does not appear to be significant at the 1 year or 2 year time horizons.

Example 4

Meningococcal, Typhoid, and Influenza Vaccines Show Anti-protective Effects Against COVID-19 at 5 Year and 2 Year Time Horizons In contrast to the previously discussed vaccines which demonstrate cross-protective effects, Meningococcal, Typhoid, and Influenza (general) vaccines were associated with increased rates of COVID-19 at 5 year and 2 year time horizons. For the Meningococcal vaccine, at the 5 year time horizon the relative risk was 1.3 (p-value: 7.6e-4), and at the 2 year time horizon the relative risk was 1.3 (p-value: 0.03). For the Typhoid vaccine, at the 5 year time horizon the relative risk was 1.6 (p-value: 2.5e-3). For the Influenza (general) vaccine, at the 5 year time horizon the relative risk was 1.1 (p-value: 0.04).

Neither the Meningococcal, Typhoid, nor Influenza (general) vaccines were expected to increase the risk of SARS-CoV-2 infection. Without being bound by any particular theory, one possible explanation is that there were some unobserved confounding variables which were correlated with these vaccines and increased risk for SARS-CoV-2 infection. For example, both Meningococcal and Typhoid vaccines were associated with international travel, which is a risk factor for COVID-19.

Example 5

Pairwise Correlation Analysis Reveals Strong Associations Between HIB, Polio, Rotavirus, Varicella, and MMR Vaccines In order to identify vaccines which may be confounding factors for other vaccines that are linked to reduced rates of SARS-CoV-2 infection, we conduct a pairwise correlation analysis. For example, it is possible that the lower rates of SARS-CoV-2 infection that we observe for one vaccine are in fact caused by another vaccine which is highly correlated with the former. To measure the correlations we use Cohen's kappa, which is a measure of correlation for categorical variables that ranges from −1 to +1. In particular, Cohen's kappa=+1 indicates that the pair of vaccines are always administered together, Cohen's kappa=0 indicates that the pair of vaccines are independent of each other, and Cohen's kappa=−1 indicates that the pair of vaccines are never administered together.

Figure 3:
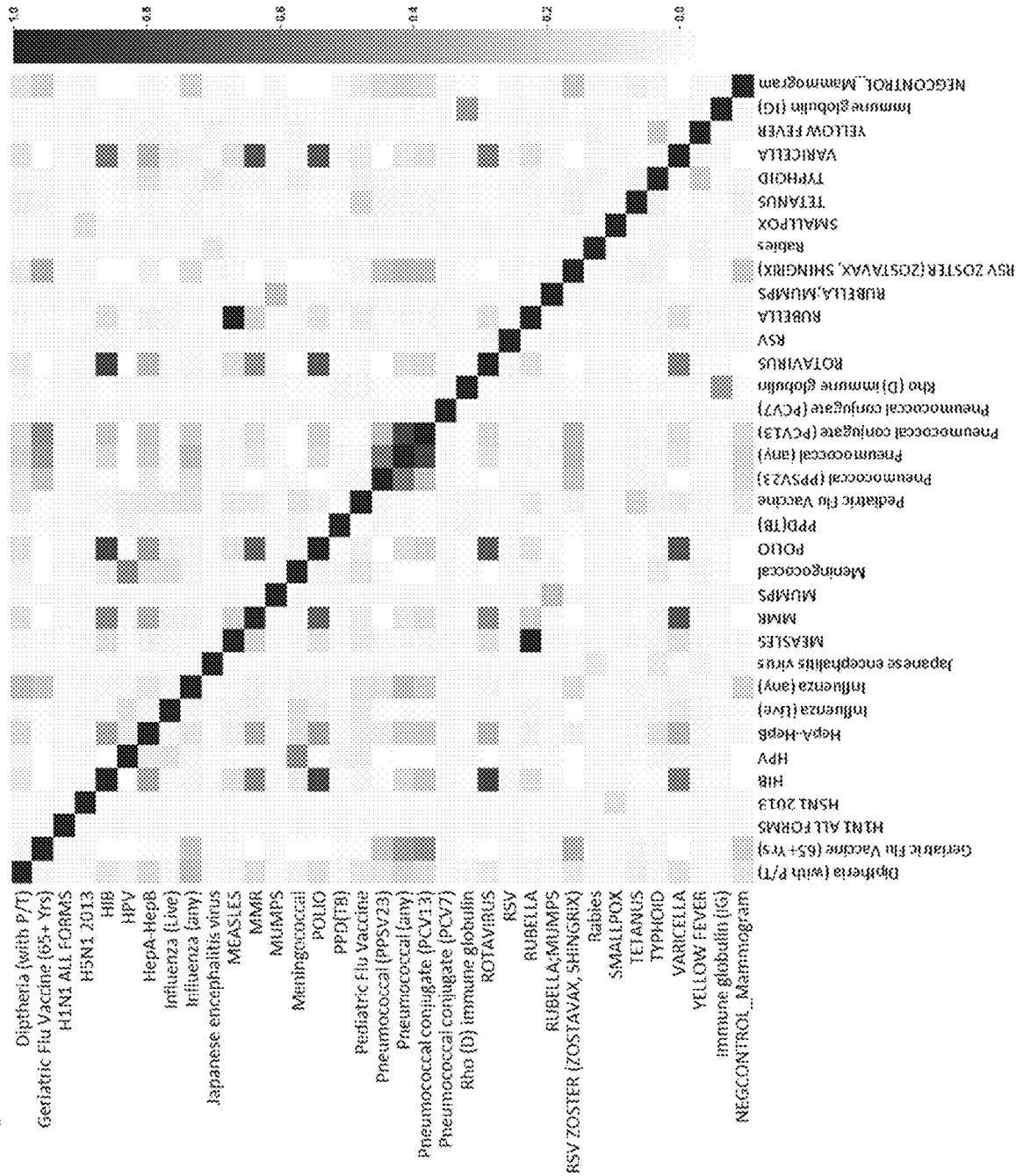
FIG. 3 shows a heatmap of correlations (inter-rater reliability) between pairs of vaccines (colored using Cohen's kappa values).

In FIG. 3, a heatmap of the pairwise correlations for each of the 26 vaccines administered in the 5 years prior to the PCR test date is shown. Sorted by Cohen's kappa value, the top vaccine-pairs with Cohen's kappa value ≥0.60 are: Measles and Rubella (Cohen's kappa: 0.99), HIB and Rotavirus (0.82), Pneumococcal (general) and PCV13 (0.81), HIB and Polio (0.80), MMR and Varicella (0.74), Polio and Varicella (0.73), Polio and Rotavirus (0.71), MMR and Polio (0.69).

Aside from the obvious pairwise correlations for (Measles, Rubella) and (Pneumococcal (general), PCV13), there was a cluster of vaccines which are routinely administered together, i.e., HIB, Polio, Rotavirus, Varicella, and MMR vaccines. The majority of patients who received this cluster of vaccines were children <18 years old (see FIG. 2). While HIB and Polio vaccines show consistent protective effects across time horizons, the Rotavirus, Varicella, and MMR vaccines show significant protective effects for particular time horizons only. This suggests that the cross-protective effects observed in this group of vaccines may be attributed to only one or a few, but not all of the vaccines in the group.

Example 5

Stratified Analysis Shows that Pneumococcal, RZV Zoster, and Polio Vaccines are Associated with Lower SARS-CoV-2 Rates in Particular Racial Subgroups In Table 12, the results of propensity score matching at the 5 year time horizon on study cohorts stratified by race is presented. Pneumococcal and RZV Zoster vaccines were linked with decreased SARS-CoV-2 rates in the Black racial subgroup. In particular, the relative risk of SARS-CoV-2 infection for black patients who have been administered Pneumococcal (general), Pneumococcal conjugate (PCV13), and RZV Zoster vaccines at the 5 year time horizon are: 0.48 (p-value: 3.6e-4), 0.42 (p-value: 3.6e-4), and 0.36 (p-value: 9.2e-3), respectively.

TABLE 12

Summary of top-10 most statistically significant (by p-value) associations between vaccination and SARS-CoV-2 rate within racial subgroups for the 5-year time horizon.

| Vaccine | Race | Total matched pairs | Vaccinated COVID+ count (rate), matched | Unvaccinated COVID+ count (rate), matched | Relative risk (95% CI) | BH-adjusted p-value |
|---|---|---|---|---|---|---|
| Pneumococcal (general) | Black | 657 | 48 (7.3%) | 101 (15.4%) | 0.48 (0.35, 0.66) | 3.3E−04 |
| Pneumococcal conjugate (PCV13) | Black | 547 | 33 (6.0%) | 78 (14.3%) | 0.42 (0.29, 0.63) | 3.3E−04 |
| *Meningococcal* | *Black* | *470* | *124 (26.4%)* | *71 (15.1%)* | *1.75 (1.34, 2.26)* | *7.0E−04* |
| *Meningococcal* | *White* | *5889* | *337 (5.7%)* | *245 (4.2%)* | *1.38 (1.17, 1.61)* | *2.1E−03* |
| RZV Zoster (ZOSTAVAX, SHINGRIX) | Black | 390 | 14 (3.6%) | 39 (10.0%) | 0.36 (0.20, 0.66) | 8.4E−03 |
| POLIO | White | 1521 | 38 (2.5%) | 70 (4.6%) | 0.54 (0.37, 0.80) | 0.03 |
| RZV Zoster (ZOSTAVAX, SHINGRIX) | Other | 428 | 16 (3.7%) | 38 (8.9%) | 0.42 (0.24, 0.75) | 0.03 |
| Diphtheria (with P/T) | White | 37872 | 1151 (3.0%) | 1289 (3.4%) | 0.89 (0.83, 0.97) | 0.05 |
| Pediatric Flu Vaccine | Black | 515 | 99 (19.2%) | 68 (13.2%) | 1.46 (1.1, 1.9) | 0.10 |
| HIB | Black | 100 | 6 (6.0%) | 17 (17.0%) | 0.35 (0.16, 0.88) | 0.20 |

* Cohorts indicating statistically significant (adjusted p-value < 0.05) associations with lower rates of SARS-CoV-2 infection are highlighted in bold, and cohorts indicating statistically significant associations with higher rates of SARS-CoV-2 infection are highlighted in italics. Summary of associations between vaccination and SARS-CoV-2 rate for age-stratified matching are shown in Table 13.

Alternatively, the Polio vaccine was linked with decreased SARS-CoV-2 rates in the White racial subgroup. For white patients who have been administered Polio vaccine in the past 5 years, the relative risk of SARS-CoV-2 infection is 0.54 (p-value: 0.03); for white patients who have been administered DPT, 0.89 (95% CI: (0.83, 0.97); p-value 0.05). However, these results may be due to the fact that the Polio vaccinated cohort overall had significantly lower rates of SARS-CoV-2 infection (see Table 6). Finally, increased rates of SARS-CoV-2 infection in the Meningococcal vaccinated cohort for both Black and White racial subgroups were observed with relative risks of 1.75 (p-value: 7.8e-4) and 1.38 (p-value: 2.3e-3), respectively. As discussed previously, this finding may be due to the fact that the Meningococcal vaccine is associated with international travel, which could be an unobserved confounding variable.

Figure 4:
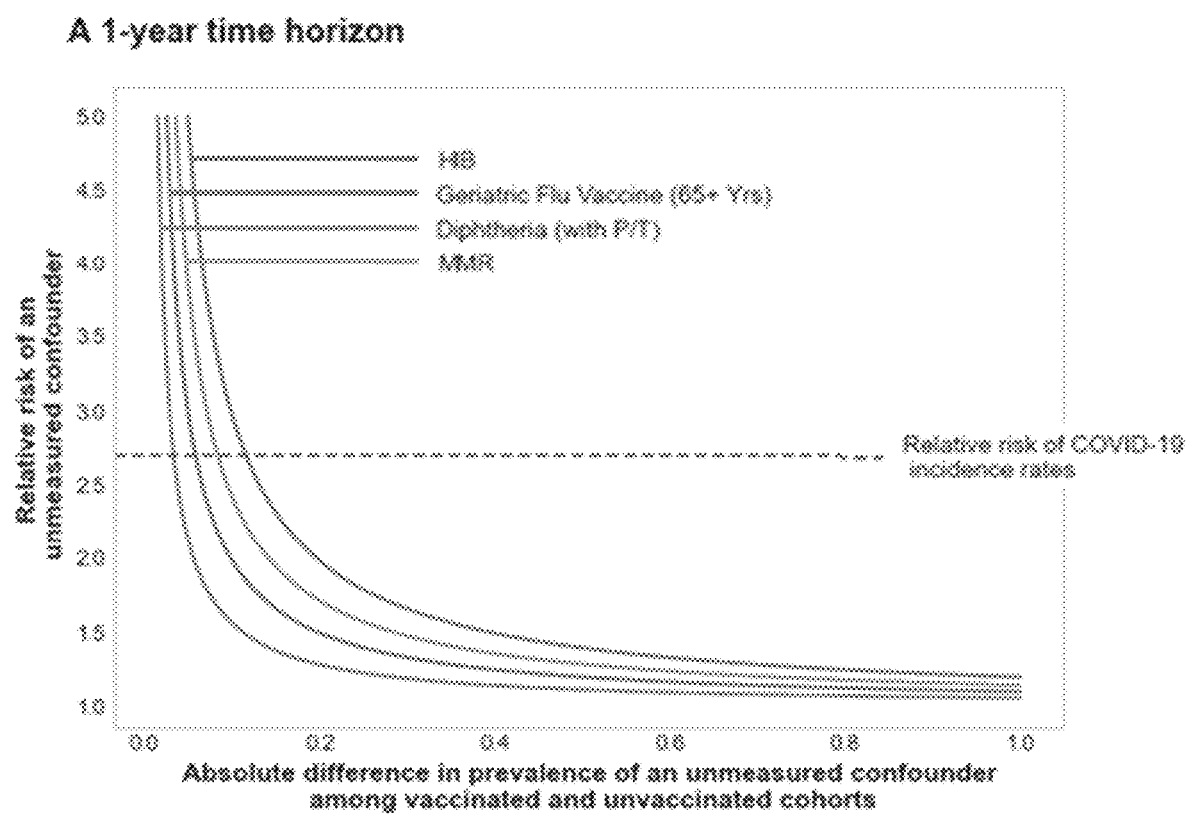
FIG. 4 shows the tipping point analysis for the cross-protective effects of vaccines with 1-year (A), 2-year (B) and 5-year (C) time horizons. For each vaccine that has a statistically significant protective effect in a particular time horizon, the (prevalence, effect size) combinations for a confounding variable that would be required to overturn the results was plotted. The x-axis indicates the absolute difference in prevalence of the confounder between vaccinated and unvaccinated (matched) cohorts. For example, if the confounding variable is present in 25% of the vaccinated cohort and 5% of the unvaccinated cohort, then the absolute difference in prevalence would be 20%. The y-axis indicates the relative ratio (effect size) of the potential unmeasured confounder. For reference, as a horizontal dotted line, the effect size of (county-level COVID-19 incidence rate≥median value) as a potential confounding variable is shown, which is 2.78. This means that patients who live in counties with greater than median COVID-19 incidence rate have an increased likelihood of SARS-CoV-2 infection by a factor of 2.78.
Figure 4:
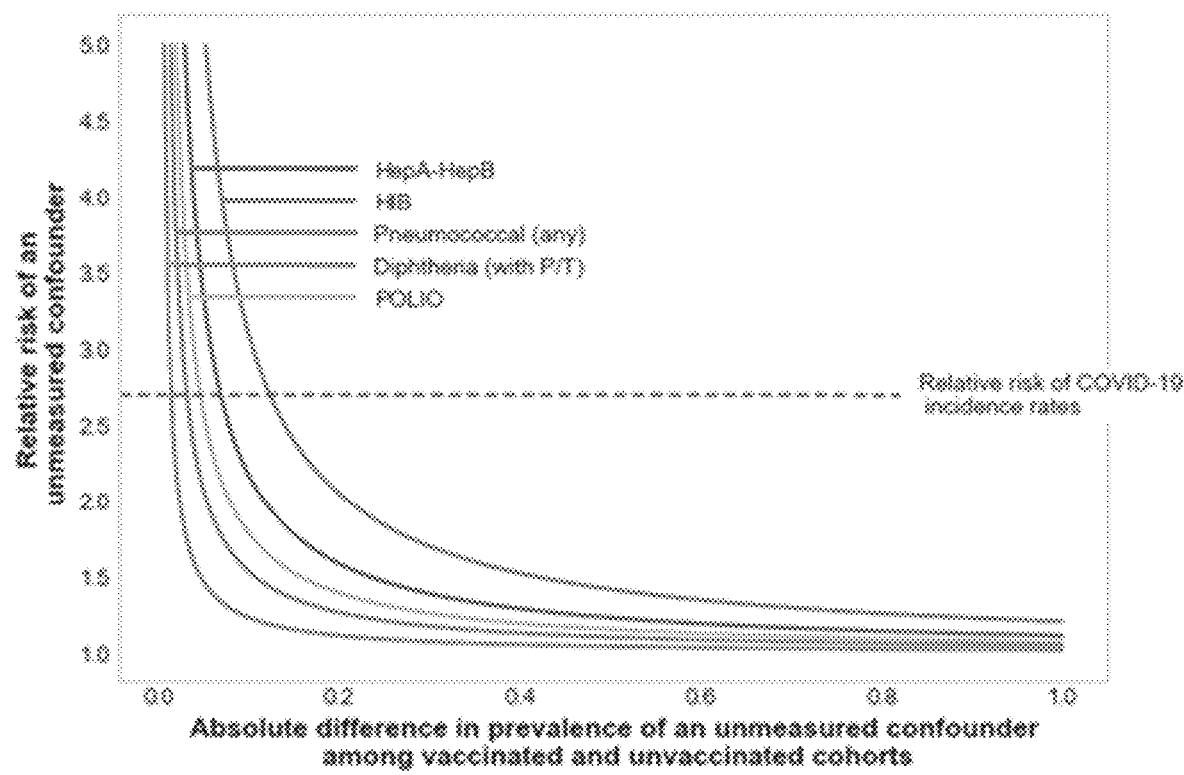
Figure 4:
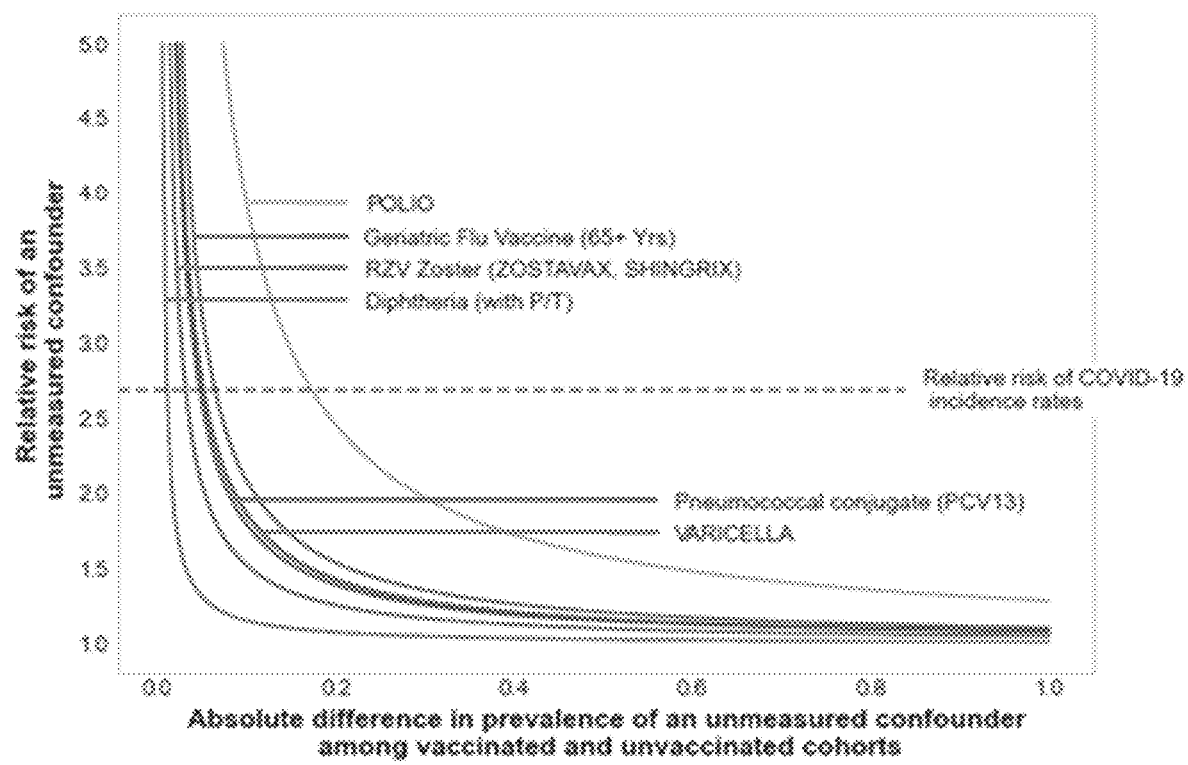

In Table 13, the results of propensity score matching at the 5 year time horizon on study cohorts stratified by age are presented. None of the (vaccine, age group) pairs showed significant differences in SARS-CoV-2 infection rates between the vaccinated and unvaccinated (matched) cohorts. These results suggest that the differential rates of SARS-CoV-2 infection between vaccinated and unvaccinated cohorts are not limited to particular age groups.

cant. There are two dimensions to consider: the effect size of confounding variable, and the relative prevalence of the confounding variable in the vaccinated and unvaccinated (matched) cohorts. In FIG. 4, the results from the Tipping Point analysis are shown for the cross-protective effects of vaccines against COVID-19. For each time horizon, the relative prevalence and effect size for an unobserved confounder that would be required to overturn the conclusion on the protective effect for that (vaccine, time horizon) pair is shown. For reference, also shown is the effect size of the covariate (county-level COVID-19 incidence rate >=median value) as a potential confounder, which has a large relative ratio of 2.78.

At the 1 year and 2 year time horizons, the cross-protective effects of the HIB vaccine were most robust to the impact of a potential confounding factor. In particular, a confounding factor with a large effect size of 2.78 would

TABLE 13

Summary of top-10 most statistically significant (by p-value) associations between vaccination and SARS-CoV-2 rate within age-range subgroups for the 5-year time horizon.

| Vaccine | Age range | Total matched pairs | Vaccinated COVIDpos count (rate), matched | Unvaccinated COVIDpos count (rate), matched | Relative risk (95% CI) | BH-adjusted p-value |
|---|---|---|---|---|---|---|
| RZV Zoster (ZOSTAVAX, SHINGRIX) | 50-64 | 6749 | 186 (2.8%) | 250 (3.7%) | 0.74 (0.62, 0.90) | 0.13 |
| Meningococcal | 19-49 | 3348 | 323 (9.6%) | 264 (7.9%) | 1.22 (1.05, 1.43) | 0.23 |
| Influenza (general) | 50-64 | 6539 | 272 (4.2%) | 217 (3.3%) | 1.25 (1.05, 1.49) | 0.23 |
| Geriatric Flu Vaccine (65+ Yrs) | 19-49 | 845 | 22 (2.6%) | 41 (4.9%) | 0.54 (0.33, 0.90) | 0.23 |
| MMR | 19-49 | 1810 | 136 (7.5%) | 101 (5.6%) | 1.35 (1.05, 1.72) | 0.23 |
| Influenza (Live) | 0-18 | 1135 | 52 (4.6%) | 78 (6.9%) | 0.67 (0.48, 0.94) | 0.23 |
| RZV Zoster (ZOSTAVAX, SHINGRIX) | 19-49 | 212 | 5 (1.4%) | 13 (5.2%) | 0.27 (0.09, 0.99) | 0.45 |
| VAC_HepA-HepB | 65+ | 2470 | 34 (1.4%) | 50 (2.0%) | 0.68 (0.44, 1.05) | 0.66 |
| VAC_Pneumococcal (PPSV23) | 19-49 | 3947 | 137 (3.5%) | 166 (4.2%) | 0.83 (0.66, 1.03) | 0.66 |
| VAC_HepA-HepB | 19-49 | 5125 | 306 (6.0%) | 268 (5.2%) | 1.14 (0.97, 1.34) | 0.66 |

Cohorts indicating statistically significant (adjusted p-value < 0.05) associations with lower rates of SARS-CoV-2 infection are highlighted in bold, and cohorts indicating statistically significant associations with higher rates of SARS-CoV-2 infection are highlighted in italics.

Example 6

Tipping Point Analysis Shows that the Observed Cross Protective Effects of HIB at the 1 and 2 Year Time Horizons and Polio Vaccine at 5 Year Time Horizon are Most Robust to Unobserved Confounders In this retrospective study, the protective effects of vaccines against SARS-CoV-2 infection were evaluated, taking into account a number of possible confounding variables, such as demographic variables and geographic COVID-19 incidence rate (see Example 1; Methods; Propensity score matching to construct negative control cohorts). However, it is possible that the results from this study have been influenced by unobserved confounders. For example, it is possible that the observed anti-protective effects for the Meningococcal, Typhoid, and Influenza (general) vaccines at the 5 year time horizon were due to confounding variables. In order to evaluate how robust the results from this study are to the effects of potential confounders, a "Tipping Point" analysis was conducted to find the point at which an unobserved confounder would "tip" the conclusion on each vaccine, making the results no longer statistically signifineed to have an absolute difference in prevalence between vaccinated and unvaccinated cohorts of 14% (16%) in order to overturn the results for the 1 year (2 year) time horizon. On the other hand, at the 5 year time horizon, the cross-protective effect of the Polio vaccine was most robust to potential confounders. A confounding factor with a large effect size of 2.78 would need to have an absolute difference in prevalence between vaccinated and unvaccinated cohorts of 19% in order to account for the protective effect here.

Example 7

Further Analysis of Vaccine Associated Clinical Characteristics and Vaccine Coverage The clinical characteristics for further vaccines (vaccinated, unvaccinated, and matched cohorts for each of these vaccines at the 5 year time horizon) are shown in Tables 14 to 16. The vaccination coverage rates for each vaccine is presented in Table 17

TABLE 14

Covariates for the 5-year Meningococcal vaccinated (matched), unvaccinated (matched), vaccinated (original) and unvaccinated (original) cohorts.

| Covariate | Mean/proportion among vaccinated (n = 7147) | Mean/proportion among unvaccinated (n = 7147) | Unmatched mean/proportion among vaccinated (n = 7147) | Unmatched mean/proportion among unvaccinated (n = 131099) |
|---|---|---|---|---|
| COVID+ rate | 7.78% | 6.09% | 7.78% | 4.18% |
| County incidence | 0.16% | 0.15% | 0.16% | 0.14% |
| County PCR test positive rate | 5.24% | 5.33% | 5.24% | 5.13% |
| Age | 24.8 | 24.6 | 24.8 | 51.2 |
| Gender - Male | 2988 (41.8%) | 2878 (40.3%) | 2988 (41.8%) | 58321 (44.5%) |
| Race - White | 5889 (82.4%) | 5731 (80.2%) | 5889 (82.4%) | 114942 (87.7%) |
| Race - Black | 470 (6.58%) | 633 (8.86%) | 470 (6.58%) | 5063 (3.86%) |
| Race - Asian | 194 (2.71%) | 208 (2.91%) | 194 (2.71%) | 3103 (2.37%) |
| Ethnicity - Hispanic | 560 (7.84%) | 532 (7.44%) | 560 (7.84%) | 7347 (5.6%) |
| Elixhauser - Hypertension | 791 (11.1%) | 949 (13.3%) | 791 (11.1%) | 48315 (36.9%) |
| Elixhauser - Pulmonary | 1607 (22.5%) | 1747 (24.4%) | 1607 (22.5%) | 29270 (22.3%) |
| Elixhauser - Diabetes mellitus | 108 (1.51%) | 126 (1.76%) | 108 (1.51%) | 6747 (5.15%) |
| Elixhauser - Diabetes mellitus (complications) | 260 (3.64%) | 388 (5.43%) | 260 (3.64%) | 11842 (9.03%) |
| Elixhauser - Coagulopathy | 487 (6.81%) | 731 (10.2%) | 487 (6.81%) | 9304 (7.1%) |
| Elixhauser - Obesity | 1123 (15.7%) | 1152 (16.1%) | 1123 (15.7%) | 33452 (25.5%) |
| Pregnancy - 90 days preceding | 150 (2.1%) | 135 (1.89%) | 150 (2.1%) | 2641 (2.01%) |
| # unique other vaccines taken over preceding 5 y | 3.55 | 3.09 | 3.55 | 2.43 |
| Propensity score | 0.75 | 0.74 | 0.75 | 0.25 |

TABLE 15

Covariates for the 5-year Typhoid vaccinated (matched), unvaccinated (matched), vaccinated (original) and unvaccinated (original) cohorts.

| Covariate | Mean/proportion among vaccinated (n = 2392) | Mean/proportion among unvaccinated (n = 2392) | Unmatched mean/proportion among vaccinated (n = 2393) | Unmatched mean/proportion among unvaccinated (n = 135853) |
|---|---|---|---|---|
| COVID+ rate | 6.27% | 3.97% | 6.27% | 4.33% |
| County incidence | 0.15% | 0.14% | 0.15% | 0.14% |
| County PCR test positive rate | 5.36% | 5.21% | 5.36% | 5.13% |
| Age | 49.3 | 48.2 | 49.3 | 49.8 |
| Gender - Male | 1025 (42.9%) | 954 (39.9%) | 1025 (42.8%) | 60284 (44.4%) |
| Race - White | 1791 (74.9%) | 1960 (81.9%) | 1791 (74.8%) | 119040 (87.6%) |
| Race - Black | 270 (11.3%) | 180 (7.53%) | 270 (11.3%) | 5263 (3.87%) |
| Race - Asian | 181 (7.57%) | 126 (5.27%) | 182 (7.61%) | 3115 (2.29%) |
| Ethnicity - Hispanic | 78 (3.26%) | 79 (3.3%) | 78 (3.26%) | 7829 (5.76%) |
| Elixhauser - Hypertension | 697 (29.1%) | 749 (31.3%) | 697 (29.1%) | 48409 (35.6%) |
| Elixhauser - Pulmonary | 477 (19.9%) | 529 (22.1%) | 477 (19.9%) | 30400 (22.4%) |
| Elixhauser - Diabetes mellitus | 107 (4.47%) | 121 (5.06%) | 108 (4.51%) | 6747 (4.97%) |
| Elixhauser - Diabetes mellitus (complications) | 141 (5.89%) | 148 (6.19%) | 141 (5.89%) | 11961 (8.8%) |
| Elixhauser - Coagulopathy | 124 (5.18%) | 143 (5.98%) | 124 (5.18%) | 9667 (7.12%) |
| Elixhauser - Obesity | 497 (20.8%) | 531 (22.2%) | 497 (20.8%) | 34078 (25.1%) |
| Pregnancy - 90 days preceding | 66 (2.76%) | 61 (2.55%) | 66 (2.76%) | 2725 (2.01%) |
| # unique other vaccines taken over preceding 5 y | 4.89 | 5.2 | 4.89 | 2.48 |
| Propensity score | 0.65 | 0.65 | 0.65 | 0.36 |

TABLE 16

Covariates for the 5-year Influenza (general) vaccinated (matched), unvaccinated (matched), vaccinated (original) and unvaccinated (original) cohorts.

| Covariate | Mean/proportion among vaccinated (n = 26682) | Mean/proportion among unvaccinated (n = 26682) | Unmatched mean/proportion among vaccinated (n = 78043) | Unmatched mean/proportion among unvaccinated (n = 60203) |
|---|---|---|---|---|
| COVID+ rate | 4.56% | 4.15% | 3.48% | 5.51% |
| County incidence | 0.15% | 0.14% | 0.13% | 0.16% |
| County PCR test positive rate | 5.24% | 4.98% | 4.82% | 5.64% |
| Age | 47.5 | 48.8 | 50.6 | 48.8 |
| Gender - Male | 12486 (46.8%) | 11661 (43.7%) | 31666 (40.6%) | 29643 (49.2%) |
| Race - White | 23275 (87.2%) | 23878 (89.5%) | 69824 (89.5%) | 51007 (84.7%) |
| Race - Black | 1122 (4.21%) | 883 (3.31%) | 2608 (3.34%) | 2925 (4.86%) |
| Race - Asian | 636 (2.38%) | 782 (2.93%) | 2025 (2.59%) | 1272 (2.11%) |
| Ethnicity - Hispanic | 1679 (6.29%) | 1468 (5.5%) | 3837 (4.92%) | 4070 (6.76%) |
| Elixhauser - Hypertension | 8504 (31.9%) | 9997 (37.5%) | 32764 (42%) | 16342 (27.1%) |
| Elixhauser - Pulmonary | 5376 (20.1%) | 6615 (24.8%) | 21722 (27.8%) | 9155 (15.2%) |
| Elixhauser - Diabetes mellitus | 1172 (4.39%) | 1153 (4.32%) | 4067 (5.21%) | 2788 (4.63%) |
| Elixhauser - Diabetes mellitus (complications) | 1955 (7.33%) | 2332 (8.74%) | 8979 (11.5%) | 3123 (5.19%) |
| Elixhauser - Coagulopathy | 1715 (6.43%) | 1865 (6.99%) | 6889 (8.83%) | 2902 (4.82%) |
| Elixhauser - Obesity | 6208 (23.3%) | 8040 (30.1%) | 24300 (31.1%) | 10275 (17.1%) |
| Pregnancy - 90 days preceding | 0.02 | 0.02 | 0.03 | 0.01 |
| # unique other vaccines taken over preceding 5 y | 1.38 | 1.27 | 3.06 | 0.57 |
| Propensity score | 0.45 | 0.46 | 0.69 | 0.31 |

TABLE 17

Vaccine coverage by time horizon and age.

| Vaccine | Time window | Total taking | Overall percent | 0-18 | 19-49 | 50-64 | 65+ |
|---|---|---|---|---|---|---|---|
| Diphtheria (with P/T) | lifetime | 89791 | 69% | 84% | 71% | 66% | 64% |
| Diphtheria (with P/T) | 5 y | 46313 | 35% | 66% | 38% | 32% | 27% |
| Diphtheria (with P/T) | 2 y | 22794 | 17% | 39% | 20% | 15% | 11% |
| Diphtheria (with P/T) | 1 y | 13151 | 10% | 25% | 12% | 8% | 6% |
| Geriatric Flu Vaccine (65+ Yrs) | lifetime | 22082 | 17% | 1% | 2% | 4% | 51% |
| Geriatric Flu Vaccine (65+ Yrs) | 5 y | 21254 | 16% | 0% | 2% | 3% | 50% |
| Geriatric Flu Vaccine (65+ Yrs) | 2 y | 17191 | 13% | 0% | 0% | 1% | 43% |
| Geriatric Flu Vaccine (65+ Yrs) | 1 y | 13132 | 10% | 0% | 0% | 0% | 33% |
| H1N1 ALL FORMS | lifetime | 19104 | 15% | 15% | 13% | 13% | 17% |
| HIB | lifetime | 19851 | 15% | 82% | 21% | 1% | 2% |
| HIB | 5 y | 4338 | 3% | 36% | 0% | 1% | 1% |
| HIB | 2 y | 2774 | 2% | 23% | 0% | 1% | 0% |
| HIB | 1 y | 2075 | 2% | 17% | 0% | 0% | 0% |
| HPV | lifetime | 13666 | 10% | 27% | 22% | 0% | 0% |
| HPV | 5 y | 5819 | 4% | 24% | 7% | 0% | 0% |
| HPV | 2 y | 2518 | 2% | 12% | 3% | 0% | 0% |
| HPV | 1 y | 1456 | 1% | 7% | 1% | 0% | 0% |
| HepA-HepB | lifetime | 44738 | 34% | 85% | 43% | 24% | 18% |
| HepA-HepB | 5 y | 14872 | 11% | 47% | 10% | 9% | 6% |
| HepA-HepB | 2 y | 8396 | 6% | 29% | 5% | 5% | 4% |
| HepA-HepB | 1 y | 5981 | 5% | 22% | 3% | 4% | 3% |
| Influenza (Live) | lifetime | 11552 | 9% | 25% | 11% | 5% | 4% |
| Influenza (Live) | 5 y | 2116 | 2% | 10% | 2% | 0% | 0% |
| Influenza (general) | lifetime | 85784 | 66% | 76% | 63% | 61% | 70% |
| Influenza (general) | 5 y | 73831 | 56% | 67% | 51% | 54% | 62% |
| Influenza (general) | 2 y | 60706 | 46% | 57% | 40% | 44% | 53% |
| Influenza (general) | 1 y | 50005 | 38% | 49% | 32% | 36% | 45% |
| MEASLES | lifetime | 13066 | 10% | 21% | 16% | 7% | 2% |
| MEASLES | 5 y | 794 | 1% | 4% | 1% | 0% | 0% |

TABLE 17-continued

Vaccine coverage by time horizon and age.

| Vaccine | Time window | Total taking | Overall percent | 0-18 | 19-49 | 50-64 | 65+ |
|---|---|---|---|---|---|---|---|
| MMR | lifetime | 31975 | 24% | 76% | 41% | 9% | 2% |
| MMR | 5 y | 6348 | 5% | 39% | 3% | 2% | 0% |
| MMR | 2 y | 3409 | 3% | 23% | 2% | 1% | 0% |
| MMR | 1 y | 2007 | 2% | 13% | 1% | 0% | 0% |
| MUMPS | lifetime | 895 | 1% | 0% | 1% | 2% | 0% |
| Meningococcal | lifetime | 15290 | 12% | 30% | 22% | 2% | 2% |
| Meningococcal | 5 y | 6643 | 5% | 26% | 6% | 1% | 1% |
| Meningococcal | 2 y | 2972 | 2% | 15% | 2% | 1% | 1% |
| Meningococcal | 1 y | 1527 | 1% | 8% | 1% | 1% | 0% |
| POLIO | lifetime | 28660 | 22% | 83% | 34% | 6% | 4% |
| POLIO | 5 y | 5431 | 4% | 47% | 1% | 1% | 1% |
| POLIO | 2 y | 3491 | 3% | 31% | 0% | 0% | 0% |
| POLIO | 1 y | 2385 | 2% | 21% | 0% | 0% | 0% |
| PPD(TB) | lifetime | 3478 | 3% | 1% | 5% | 2% | 1% |
| PPD(TB) | 5 y | 2409 | 2% | 1% | 4% | 1% | 1% |
| PPD(TB) | 2 y | 1674 | 1% | 1% | 2% | 1% | 0% |
| PPD(TB) | 1 y | 916 | 1% | 0% | 1% | 0% | 0% |
| Pediatric Flu Vaccine | lifetime | 12044 | 9% | 17% | 12% | 10% | 4% |
| Pediatric Flu Vaccine | 5 y | 10912 | 8% | 16% | 11% | 9% | 3% |
| Pneumococcal (PPSV23) | lifetime | 38415 | 29% | 2% | 13% | 27% | 59% |
| Pneumococcal (PPSV23) | 5 y | 16607 | 13% | 1% | 8% | 13% | 22% |
| Pneumococcal (PPSV23) | 2 y | 8883 | 7% | 1% | 4% | 7% | 11% |
| Pneumococcal (PPSV23) | 1 y | 4948 | 4% | 1% | 3% | 4% | 6% |
| Pneumococcal (general) | lifetime | 52362 | 40% | 81% | 18% | 30% | 66% |
| Pneumococcal (general) | 5 y | 33351 | 25% | 36% | 9% | 19% | 49% |
| Pneumococcal (general) | 2 y | 15552 | 12% | 24% | 6% | 11% | 18% |
| Pneumococcal (general) | 1 y | 9367 | 7% | 18% | 3% | 7% | 10% |
| Pneumococcal conjugate (PCV13) | lifetime | 33083 | 25% | 56% | 4% | 12% | 56% |
| Pneumococcal conjugate (PCV13) | 5 y | 24731 | 19% | 36% | 3% | 10% | 43% |
| Pneumococcal conjugate (PCV13) | 2 y | 8183 | 6% | 23% | 2% | 5% | 9% |
| Pneumococcal conjugate (PCV13) | 1 y | 4785 | 4% | 17% | 1% | 3% | 4% |
| Pneumococcal conjugate (PCV7) | lifetime | 5365 | 4% | 33% | 4% | 0% | 1% |
| RHo (D) immune globulin | lifetime | 1302 | 1% | 0% | 3% | 0% | 0% |
| RHo (D) immune globulin | 5 y | 881 | 1% | 0% | 2% | 0% | 0% |
| ROTAVIRUS | lifetime | 5630 | 4% | 53% | 0% | 0% | 0% |
| ROTAVIRUS | 5 y | 3031 | 2% | 30% | 0% | 0% | 0% |
| ROTAVIRUS | 2 y | 1739 | 1% | 17% | 0% | 0% | 0% |
| ROTAVIRUS | 1 y | 1162 | 1% | 12% | 0% | 0% | 0% |
| RUBELLA | lifetime | 12276 | 9% | 21% | 16% | 6% | 1% |
| RUBELLA | 5 y | 783 | 1% | 4% | 1% | 0% | 0% |
| RUBELLA; MUMPS | lifetime | 1366 | 1% | 0% | 1% | 3% | 0% |
| RZV Zoster (ZOSTAVAX, SHINGRIX) | lifetime | 24993 | 19% | 0% | 0% | 22% | 46% |
| RZV Zoster (ZOSTAVAX, SHINGRIX) | 5 y | 16692 | 13% | 0% | 0% | 20% | 26% |
| RZV Zoster (ZOSTAVAX, SHINGRIX) | 2 y | 14028 | 11% | 0% | 0% | 18% | 21% |
| RZV Zoster (ZOSTAVAX, SHINGRIX) | 1 y | 9634 | 7% | 0% | 0% | 14% | 13% |
| Rabies | lifetime | 994 | 1% | 0% | 1% | 1% | 0% |
| TETANUS | lifetime | 19321 | 15% | 0% | 14% | 16% | 19% |
| TETANUS | 5 y | 2645 | 2% | 0% | 2% | 3% | 2% |
| TYPHOID | lifetime | 5230 | 4% | 1% | 4% | 4% | 5% |
| TYPHOID | 5 y | 2261 | 2% | 1% | 2% | 2% | 2% |
| TYPHOID | 2 y | 1010 | 1% | 0% | 1% | 1% | 1% |
| VARICELLA | lifetime | 18335 | 14% | 75% | 20% | 2% | 1% |
| VARICELLA | 5 y | 5353 | 4% | 40% | 2% | 0% | 0% |
| VARICELLA | 2 y | 2853 | 2% | 23% | 1% | 0% | 0% |
| VARICELLA | 1 y | 1670 | 1% | 14% | 1% | 0% | 0% |
| YELLOW FEVER | lifetime | 1894 | 1% | 1% | 1% | 1% | 2% |
| immune globulin (IG) | lifetime | 900 | 1% | 0% | 1% | 0% | 0% |

Example 8

Mammogram and Colon Screen Used as Negative Controls Show Significant Associations with Lower Rates of SARS-CoV-2 Infection on Unmatched Cohorts and are not Statistically Significant on Matched Cohorts In order to verify the efficacy of propensity score matching procedure, we compute associations between a set of negative controls: mammogram and colon screen with lower rates of SARS-CoV-2 infection on both matched (after propensity score matching) and unmatched cohorts. We observe that mammogram is significantly associated with lower rates of SARS-CoV-2 infection with risk ratios of 0.49 (p-value: 1.3e-45), 0.53 (p-value: 8.1e-54) and 0.53 (p-value: 6.6e-60) on unmatched cohorts for 1 year, 2 year and 5 year time horizons, respectively. However, after propensity score matching, the associations are not statistically significant with risk ratios of 0.85 (p-value: 0.05), 0.94 (p-value: 0.41) and 0.99 (p-value: 0.95) on unmatched cohorts for 1 year, 2 year and 5 year time horizons, respectively.

Similarly, colon screen is significantly associated with lower rates of SARS-CoV-2 infection with risk ratios of 0.46 (p-value: 8.2e-21), 0.50 (p-value: 6.9e-30) and 0.53 (p-value: 9.5e-56) on unmatched cohorts for 1 year, 2 year and 5 year time horizons, respectively. However, after propensity score matching, the associations are not statistically significant with risk ratios of 0.94 (p-value: 0.62), 0.93 (p-value: 0.40) and 1.0 (p-value: 0.98) on unmatched cohorts for 1 year, 2 year and 5 year time horizons, respectively. In Table 3, we present associations between negative controls and lower rates of SARS-CoV-2 infection. Ongoing clinical studies offer preliminary evidence that existing vaccines may reduce risk of SARS-CoV-2 infection. For example, interim results from the ACTIVATE trial 11 indicate that the BCG vaccine reduces SARS-CoV-2 infection rates up to 53%. While specific vaccines such as BCG are being tested for cross-protective effects against SARS-CoV-2 infection based on their prior potential for protection against other diseases 13, to our knowledge, a systematic hypothesis-free analysis to identify potential vaccines that can have beneficial effects against SARS-CoV-2 infection is lacking. Our retrospective study has systematically analysed 19 different vaccines and identified key vaccines that are correlated with lower-rates of SARS-CoV-2 infection, after controlling for confounding factors (see Results). In particular, we find that patients with These vaccines are promising candidates for follow-up pre-clinical animal studies and clinical trials.

Due to the retrospective nature of this study, there are multiple types of biases which may have impacted the findings from this statistical analysis. For example, there is possible confounding variable bias, which is the motivation for using propensity score matching to construct negative control cohorts (see Methods). Although we take into consideration many potential confounding variables in the covariate balancing step of the propensity score matching algorithm, there may still be additional unobserved confounding variables that we have left out. For example, socioeconomic status is a risk factor for exposure to SARS-CoV-2 infection that we do not explicitly account for in this study. In the tipping point analysis, we estimate the effect size and prevalence of an unobserved confounder which would be required to overturn the statistically significant findings (see FIG. 4). Even among the variables that we consider, there is potential for bias if the cohorts are poorly matched on those covariates. In Tables 7-16, we present the propensity score matching results for a number of vaccines at the 5 year time horizon, in order to show the matching quality for each of these statistical comparisons.

In addition, it is possible that the study design has introduced a source of bias. For example, the vaccinated individuals in the Mayo Clinic dataset may have a higher baseline likelihood of being tested for SARS-CoV-2, which would result in collider bias14. In this case, we may observe artificially low SARS-CoV-2 infection rates among the vaccinated cohorts due to the "healthy user effect".[15] We have run several experiments on "negative control" clinical covariates including breast cancer and colon cancer screening which suggest that the statistical analysis is effective in filtering out spurious associations between SARS-CoV-2 rate and clinical covariates which may be driven by the healthy user effect. This result bolsters the claim that the associations between vaccination history and decreased SARS-CoV-2 infection rates are driven by underlying immunologic mechanisms rather than behavioral patterns of healthy individuals.

As one of the initial studies linking historical vaccination records to an exploratory retrospective analysis, more research is warranted in order to confirm the findings. We plan to update this analysis in coming months as more SARS-CoV-2 PCR testing data becomes available. It must be noted that this study is based on the patient data from one academic medical center from the US, which restricts the analysis to vaccines administered in this geographic region. The findings from here should warrant undertaking similar studies from hospitals across the world.

REFERENCES

1. Thanh Le, T. et. al. The COVID-19 vaccine development landscape. Nat. Rev. Drug Discov. 19, 305-306 (2020).
2. Pronker, E. S., Weenen, T. C., Commandeur, H., Eric H J H & Albertus D M. Risk in Vaccine Research and Development Quantified. PLoS One 8, e57755 (2013).
3. Lurie, N., Saville, M., Hatchett, R. & Halton, J. Developing Covid-19 Vaccines at Pandemic Speed. N. Engl. J. Med. 382, 1969-1973 (2020).
4. Sánchez-Ramón, S. et. al. Trained Immunity-Based Vaccines: A New Paradigm for the Development of Broad-Spectrum Anti-infectious Formulations. Front. Immunol. 9, (2018).
5. Curtis, N., Sparrow, A., Ghebreyesus, T. A. & Netea, M. G. Considering BCG vaccination to reduce the impact of COVID-19. Lancet 395, 1545-1546 (2020).
6. Chumakov, K., Benn, C. S., Aaby, P., Kottilil, S. & Gallo, R. Can existing live vaccines prevent COVID-19? Science 368, 1187-1188 (2020).
7. OPV as Potential Protection Against COVID-19—Full Text View—ClinicalTrials.gov. clinicaltrials.gov/ct2/show/NCT04445428.
8. Measles Vaccine in HCW—Full Text View—ClinicalTrials.gov. clinicaltrials.gov/ct2/show/NCT04357028.
9. Influenza Vaccination, ACEI and ARB in the Evolution of SARS-Covid19 Infection—Full Text View—ClinicalTrials.gov.clinicaltrials.gov/ct2/show/NCT04367883.
10. BCG Vaccination for Healthcare Workers in COVID-19 Pandemic—Full Text View—ClinicalTrials.gov.clinicaltrials.gov/ct2/show/NCT04379336.
11. Bacillus Calmette-guérin Vaccination to Prevent COVID-19—Full Text View—ClinicalTrials.gov.clinicaltrials.gov/ct2/show/NCT04414267.

12. BCG Vaccination to Protect Healthcare Workers Against COVID-19—Full Text View—ClinicalTrials.gov.clinicaltrials.gov/ct2/show/NCT04327206.
13. BCG Vaccine for Health Care Workers as Defense Against COVID 19—Full Text View—ClinicalTrials-.gov.clinicaltrials.gov/ct2/show/NCT04348370.
14. Griffith, G. et. al. Collider bias undermines our understanding of COVID-19 disease risk and severity. medRxiv 2020.05.04.20090506 (2020).
15. Shrank, W. H., Patrick, A. R. & Alan Brookhart, M. Healthy User and Related Biases in Observational Studies of Preventive Interventions: A Primer for Physicians. J. Gen. Intern. Med. 26, 546 (2011).
16. Elixhauser, A., Steiner, C., Robert Harris, D. & Coffey, R. M. Comorbidity Measures for Use with Administrative Data. Medical Care vol. 36 8-27 (1998).
17. Davis, L. Corona Data Scraper. coronadatascraper.com/#home.
18. Austin, P. C. An Introduction to Propensity Score Methods for Reducing the Effects of Confounding in Observational Studies. Multivariate Behay. Res. 46, 399 (2011).
19. Pedregosa, F. et. al. Scikit-learn: Machine Learning in Python. J. Mach. Learn. Res. 12, 2825-2830 (2011).
20. Austin, P. C. Optimal caliper widths for propensity-score matching when estimating differences in means and differences in proportions in observational studies. Pharm. Stat. 10, 150-161 (2011).
21. Benjamini, Y. & Hochberg, Y. Controlling the False Discovery Rate: A Practical and Powerful Approach to Multiple Testing. Journal of the Royal Statistical Society: Series B (Methodological) vol. 57 289-300 (1995).
22. Assessing the Sensitivity of Regression Results to Unmeasured Confounders in Observational Studies on JSTOR. www.jstor.org/stable/2533848?seq=1.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A method for reducing the risk of a subject acquiring or fully presenting a disease case by SARS-CoV-2 infection, comprising:
    determining a plurality of demographic covariates of the subject, wherein
        determining the plurality of demographic covariates comprises:
        determining a propensity score for the subject; and
        generating at least a negative cohort as a function of the propensity score;
    identifying one or more vaccines not administered to the subject within the past 1 year, the one or more vaccines not having been administered to the subject within the past 1 year selected from a group comprising a haemophilus influenzae type B (Hib) vaccine, an influenza vaccine, a diphtheria-pertussis-tetanus vaccine, and a measles-mumps-rubella vaccine using a logistic regression model as a function of the plurality of demographic covariates of the subject and the propensity score; and
    administering to the subject at least one of the one or more vaccines identified as not having been administered to the subject within the past 1 year.

2. The method of claim 1, wherein the method induces a heterologous immune response to a SARS-CoV-2 infection in a subject.

3. A method for reducing the risk of a subject acquiring or fully presenting a disease case by SARS-CoV-2 infection, comprising:
    determining a plurality of demographic covariates of the subject, wherein
        determining the plurality of demographic covariates comprises:
        determining a propensity score for the subject; and
        generating at least a negative cohort as a function of the propensity score;
    identifying one or more vaccines not having been administered to the subject within the past 2 years, wherein the one or more vaccines not having been administered to the subject within the past 2 years are selected from a group comprising a hepatitis B vaccine, a haemophilus influenzae type B (Hib) vaccine, a diphtheria-pertussis-tetanus vaccine, or a polio vaccine using a logistic regression model as a function of the plurality of demographic covariates of the subject and the propensity score; and
    administering to the subject at least one of the one or more vaccines not administered to the subject within the past 2 years.

4. The method of claim 3, wherein the method induces a heterologous immune response to a SARS-CoV-2 infection in a subject.

5. A method for reducing the risk of a subject acquiring or fully presenting a disease case by SARS-CoV-2 infection, comprising;
    determining a plurality of demographic covariates of the subject, wherein
        determining the plurality of demographic covariates comprises:
        determining a propensity score for the subject; and
        generating at least a negative cohort as a function of the propensity score;
    identifying one or more vaccines not having been administered to the subject within the past 2 years, the one or more vaccines not having been administered to the subject within the past 2 years selected from a group comprising a polio vaccine, an influenza vaccine, a varicella-zoster virus (VZV) vaccine, and a diphtheria-pertussis-tetanus vaccine using a logistic regression model as a function of the plurality of demographic covariates of the subject and the propensity score; and
    administering to the subject at least one of the one or more vaccines identified as not having been administered to the subject within the past 2 years.

6. The method of claim 5, wherein the method induces a heterologous immune response to a SARS-CoV-2 infection in a subject.

7. The method of claim 1, comprising administering a diphtheria-pertussis-tetanus vaccine, or a measles-mumpsrubella combination vaccine if one or more vaccines is identified as not having been administered to the subject within the past 1 year.

8. A method for the identification and stratification of a subject at risk of SARS-CoV-2 infection comprising;
   determining a plurality of demographic covariates of the subject, wherein
      determining the plurality of demographic covariates comprises:
      determining a propensity score for the subject; and
      generating at least a negative cohort as a function of the propensity score;
   identifying one or more vaccines not administered to the subject within the past 5 years, the one or more vaccines not having been administered to the subject within the past 5 years selected from a group comprising polio vaccine, an influenza vaccine, a varicella-zoster virus (VZV) vaccine, and a diphtheria-pertussis-tetanus vaccine using a logistic regression model as a function of the plurality of demographic covariates of the subject and the propensity score; and
   if said subject is stratified into an at risk population and identified as not having received at least one of the one or more vaccines not administered to the subject within the past 5 years, administering to the subject at least one of the one or more vaccines not administered to the subject within the past 5 years.

9. The method of claim 8, wherein the subject is stratified by at least one demographic covariate, wherein said demographic covariates comprise age, race, ethnicity, gender, or any combination thereof.

10. The method of claim 8, wherein the subject is Black, and the vaccine to be administered is varicella zoster virus (VZV) vaccine.

11. The method of claim 8, wherein the subject is White, and the vaccine to be administered is an influenza vaccine or a polio vaccine.

12. The method of claim 8, wherein the race of the subject is reported as Other, wherein Other is any race other than White, Black, or Asian, and the vaccine to be administered is varicella zoster virus (VZV) vaccine.

13. The method of claim 8, wherein the subject is less than 50 years old, and the vaccine to be administered is an influenza vaccine.

14. The method of claim 13, wherein the subject is from 19 years old to 49 years old.

15. The method of claim 1, wherein the subject is an essential or critical infrastructure worker, selected from a teacher, childcare provider, healthcare worker, caregiver, law enforcement officer, public safety officer, first responder, or food and agriculture worker.

16. The method of claim 9, wherein the stratification is according to age brackets, wherein the age brackets are ≤18 years old, 19 to 49 years old, 50 to 64 years old, 65+ years old, or any combination thereof.

* * * * *